United States Patent [19]

Gruber et al.

[11] Patent Number: 5,807,973
[45] Date of Patent: *Sep. 15, 1998

[54] MELT-STABLE LACTIDE POLYMER NONWOVEN FABRIC AND PROCESS FOR MANUFACTURE THEREOF

[75] Inventors: Patrick Richard Gruber, St. Paul; Jeffrey John Kolstad, Wayzata; Christopher M. Ryan, Dayton; Eric Stanley Hall, Crystal; Robin Sue Eichen Conn, Minneapolis, all of Minn.

[73] Assignee: Cargill, Incorporated, Minneapolis, Minn.

[ * ] Notice: The term of this patent shall not extend beyond the expiration date of Pat. No. 5,525,706.

[21] Appl. No.: 534,560

[22] Filed: Sep. 27, 1995

Related U.S. Application Data

[63] Continuation of Ser. No. 328,550, Oct. 25, 1994, Pat. No. 5,525,706, which is a continuation of Ser. No. 71,590, Jun. 2, 1993, abandoned, which is a continuation-in-part of Ser. No. 955,690, Oct. 2, 1992, Pat. No. 5,338,822.

[51] Int. Cl.$^6$ .................................................. C08G 63/08
[52] U.S. Cl. ........................... 528/354; 528/361; 525/408; 525/413; 525/415; 428/224; 428/283; 428/288; 428/480
[58] Field of Search ..................................... 528/354, 361; 525/408, 413, 415; 428/480, 224, 283, 288

[56] References Cited

U.S. PATENT DOCUMENTS

| | | | |
|---|---|---|---|
| 1,095,205 | 5/1914 | Gr ter et al. | 528/354 |
| 1,849,107 | 3/1932 | Moss | 528/354 |
| 1,995,970 | 4/1935 | Dorough | 528/354 |

(List continued on next page.)

FOREIGN PATENT DOCUMENTS

| | | |
|---|---|---|
| 808731 | 3/1969 | Canada . |
| 863673 | 2/1971 | Canada . |
| 923245 | 3/1973 | Canada . |
| 2057667 | 12/1991 | Canada . |
| 2057668 | 12/1991 | Canada . |
| 2057669 | 12/1991 | Canada . |

(List continued on next page.)

OTHER PUBLICATIONS

T.M. Jackanicz, "Polyactic Acid as a Biodegradable Carrier for Contraceptive Steroids", *Contraception*, vol. 8, No. 3, 227–234 (1973).

A.D. Schwope et al. "Lactic/Glycolic Acid Polymers as Narcotic Antagonist Delivery Systems", *Life Sciences*, vol. 17, 1877–1886 (1975).

L.C. Anderson, "An Injectable Sustained Release Fertility Control System", *Contraception*, vol. 13, No. 3, 375–384 (1976).

W. Carothers, G. Dorough, and F. Van Natta ("Studies of Polymerization and Ring Formation. X. The Reversible Polymerization of Six–Membered Cyclic Esters", 1932, *American Chemical Society Journal*, v. 54, pp. 761–772).

E. Filachione, E. Costello, T. Dietz and C. Fisher ("Lactic Acid Derivatives as Plasticizers Esters of Polymeric Lactic Acid", 1951, *Bur. Agric. Ind. Chem.*, v. 11, pp. 1–11).

D. Deane and E. Hammond ("Coagulation of Milk for Cheese–Making by Ester Hydrolysis", 1960, *Journal of Dairy Science*, v. 43, pp. 1421–1429).

Kulkarni et al. ("Biodegradable Poly(lactic acid) Polymers", 1971, *J. Biomed. Mater. Res.*, v. 5, pp. 169–181).

A. Schindler, R. Jeffcoat, G. Kimmel, C. Pitt, M. Wall and R. Zweidinnger ("Biodegradable Polymers for sustained Drug Delivery", 1977, *Contemporary Topics in Polymer Science*, v. 2, pp. 251–287).

I. Luderwalk ("Thermal Degradation of Polyesters in the Mass Spectrometer", 1979, *Dev. Polymer Degradation*, v. 2, pp. 77–98.

M. Vert and F. Chabot ("Stereoregular Bioresorbable Polyesters for Orthopaedic Surgery", 1981, *Makromol. Chem.*, Supp. 5, pp. 30–41).

M. Gupta and V. Deshmukh ("Thermal Oxidative Degradation of Poly–lactic Acid; Part I: Activation Energy of Thermal Degradation in Air", 1982, *Colloid & Polymer Science*, v. 260, pp. 308–311).

M. Gupta and V. Deshmukh ("Thermal Oxidative Degradation of Poly–lactic Acid; Part II: Molecular Weight and Electronic Spectra During Isothermal Heating", 1982, *Colloid & Polymer Science*, v. 260, pp. 514–517).

D.L. Wise et al., "Sustained Release of an Antimalarial Drug Using a Copolymer of Glycolic/Lactic Acid", *Life Sciences*, vol. 19, 867–874 (1976).

R.A. Miller et al., "Degradation Rates of Resorbable Implants (Polylactates and Polyglycolates): Rate Modification with Changes in Pla/Pga Copolymer Rations", *J. Biomed. Mater. Res.*, vol. 11, 711–719 (1977).

D.K. Gilding et al., Biodegradable Polymers for Use in Surgery —Polyglycolic/Polylactic Acid Homo and Copolymers: 1. *Polymer*, vol. 2, 1459–1464 (1979).

D.K. Gilding, "Degradation of Polymers: Mechanisms and Implications for Biomedical Applications", *Biocompatibility of Clinical Implant Materials*, D.F. Williams, ed., vol. 1, 43–65 (1981).

(List continued on next page.)

*Primary Examiner*—P. Hampton-Hightower
*Attorney, Agent, or Firm*—Merchant, Gould, Smith, Edell, Welter & Schmidt, P.A.

[57] ABSTRACT

A nonwoven fabric comprised of a lactide polymer. The lactide polymer comprises a plurality of poly(lactide) polymer chains, residual lactide in concentration of less than about 2 percent and water in concentration of less than about 2000 parts-per-million. A process for manufacturing a nonwoven fabric with the lactide polymer composition is also disclosed.

22 Claims, 3 Drawing Sheets

U.S. PATENT DOCUMENTS

| | | | |
|---|---|---|---|
| 2,396,994 | 3/1946 | Filachione et al. | 528/354 |
| 2,703,316 | 3/1955 | Schneider | 528/354 |
| 2,758,987 | 8/1956 | Salzberg | 528/354 |
| 2,951,828 | 9/1960 | Zeile et al. | 528/354 |
| 3,268,487 | 8/1966 | Klootwijk | 528/354 |
| 3,322,791 | 5/1967 | Selman | 528/354 |
| 3,531,561 | 9/1970 | Trehu | 264/210 |
| 3,636,956 | 1/1972 | Schneider | 128/335.5 |
| 3,772,420 | 11/1973 | Glick et al. | 264/102 |
| 3,773,919 | 11/1973 | Boswell et al. | 424/19 |
| 3,839,297 | 10/1974 | Wassermann et al. | 528/354 |
| 3,887,699 | 6/1975 | Yolles | 424/19 |
| 3,912,692 | 10/1975 | Casey et al. | 328/354 |
| 4,045,418 | 8/1977 | Sinclair | 528/354 |
| 4,249,531 | 2/1981 | Heller et al. | 128/260 |
| 4,273,920 | 6/1981 | Nevin | 528/361 |
| 4,279,249 | 7/1981 | Vert et al. | 128/92 |
| 4,441,496 | 4/1984 | Shalaby et al. | 528/354 |
| 4,595,713 | 6/1986 | St. John | 523/105 |
| 4,643,734 | 2/1987 | Lin | 623/16 |
| 4,677,191 | 6/1987 | Tanaka et al. | 528/361 |
| 4,683,288 | 7/1987 | Tanaka et al. | 528/361 |
| 4,719,246 | 1/1988 | Murdoch et al. | 521/134 |
| 4,727,163 | 2/1988 | Bellis | 549/274 |
| 4,728,721 | 3/1988 | Yamamoto et al. | 528/361 |
| 4,766,182 | 8/1988 | Murdoch et al. | 525/413 |
| 4,789,726 | 12/1988 | Hutchinson | 528/354 |
| 4,797,468 | 1/1989 | DeVries | 528/254 |
| 4,800,219 | 1/1989 | Murdoch et al. | 525/413 |
| 4,835,293 | 5/1989 | Bhatia | 549/274 |
| 4,902,515 | 2/1990 | Lomis et al. | 424/486 |
| 4,950,258 | 8/1990 | Kawai et al. | 604/281 |
| 4,960,866 | 10/1990 | Bendix et al. | 528/499 |
| 4,981,696 | 1/1991 | Loomis et al. | 424/486 |
| 4,983,745 | 1/1991 | Muller et al. | 549/274 |
| 4,990,222 | 2/1991 | Aigner et al. | 203/91 |
| 5,011,946 | 4/1991 | Hess et al. | 549/274 |
| 5,023,349 | 6/1991 | Bhatia | 549/274 |
| 5,023,350 | 6/1991 | Bhatia | 549/274 |
| 5,041,529 | 8/1991 | Shinoda et al. | 528/354 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,076,983 | 12/1991 | Loomis et al. | 264/101 |
| 5,097,005 | 3/1992 | Tietz | 528/354 |
| 5,108,399 | 4/1992 | Eitenmuller et al. | 606/77 |
| 5,132,397 | 7/1992 | DeGuia | 528/354 |
| 5,134,171 | 7/1992 | Hammel et al. | 521/98 |
| 5,136,017 | 8/1992 | Kharas et al. | 528/354 |
| 5,136,057 | 8/1992 | Bhatia | 549/274 |
| 5,142,023 | 8/1992 | Gruber et al. | 528/354 |
| 5,149,833 | 9/1992 | Hess et al. | 549/274 |
| 5,180,765 | 1/1993 | Sinclair | 528/354 |
| 5,210,296 | 5/1993 | Cockrem et al. | 562/589 |
| 5,229,528 | 7/1993 | Brake et al. | 549/274 |
| 5,236,560 | 8/1993 | Drysdale et al. | 203/99 |
| 5,294,469 | 3/1994 | Suzuki et al. | 428/36.1 |
| 5,338,822 | 8/1994 | Gruber et al. | 528/354 |
| 5,359,026 | 10/1994 | Gruber | 428/480 |
| 5,475,080 | 12/1995 | Gruber et al. | 428/480 |
| 5,484,881 | 1/1996 | Gruber et al. | 528/354 |
| 5,525,706 | 6/1996 | Gruber et al. | 528/354 |

FOREIGN PATENT DOCUMENTS

| | | |
|---|---|---|
| 0299730 | 1/1989 | European Pat. Off. . |
| 0314245 | 5/1989 | European Pat. Off. . |
| 0052510 | 3/1992 | European Pat. Off. . |
| 0481732 | 4/1992 | European Pat. Off. . |
| 0507554 | 10/1992 | European Pat. Off. . |
| 0510998 | 10/1992 | European Pat. Off. . |
| 0515203 | 11/1992 | European Pat. Off. . |
| 0532154 | 3/1993 | European Pat. Off. . |
| 0533314 | 3/1993 | European Pat. Off. . |
| 540182 | 5/1993 | European Pat. Off. . |
| 597427 | 5/1994 | European Pat. Off. . |
| 267826 | 12/1913 | Germany . |
| 1083275 | 12/1960 | Germany . |
| 1543958 | 2/1970 | Germany . |
| OS3632103 | 3/1988 | Germany . |
| 69015789 | 11/1964 | Japan . |
| 0107591 | 2/1984 | Japan . |
| 4-283227 | of 1992 | Japan . |
| 1040168 | 4/1968 | United Kingdom . |
| 1108720 | 4/1968 | United Kingdom . |
| 1351409 | 5/1974 | United Kingdom . |
| 2145422 | 3/1985 | United Kingdom . |
| WO90/01521 | 2/1990 | WIPO . |
| WO91/02015 | 2/1991 | WIPO . |
| WO91/06601 | 5/1991 | WIPO . |
| WO92/00292 | 1/1992 | WIPO . |
| WO92/00974 | 1/1992 | WIPO . |
| WO92/04410 | 3/1992 | WIPO . |
| WO92/04412 | 3/1992 | WIPO . |
| WO92/04413 | 3/1992 | WIPO . |
| WO92/05167 | 4/1992 | WIPO . |
| WO92/05168 | 4/1992 | WIPO . |
| WO92/05311 | 4/1992 | WIPO . |
| WO92/15340 | 9/1992 | WIPO . |
| WO91/17155 | 11/1992 | WIPO . |
| WO9300568 | 1/1993 | WIPO . |
| WO 93/02075 | 2/1993 | WIPO |

OTHER PUBLICATIONS

A.M. Reed and D.K. Gilding, "Biodegradable Polymers for Use in Surgery Polyglycolic/Polylactic Acid Homo and Copolymers: 2. In Vitro Degradation", *Polymer*, vol. 22, No. 4, 494–498 (1981).

D.K. Gilding, "biodegradable Polymers" *Biocompatibility of Clinical Implant Materials*, D.F. Williams, ed., vol. 2, 209–232 (1981).

J.D. Strobel, "Biodegradable Polymers", paper presented at Medical Textiles and Biomedical Polymers and Materials Conference held at Clemson, S.C., U.S.A., Dec. 5–6, 1989, Stolle Research and Development Corp., PD 712–01, pp. 1–32 and Attachments A1–A21.

"Biocompatible Composite Would Be Completely Absorbed in the Body", *Advanced Materials*, vol. 12, No. 15, Aug. 1990, p. 6.

"Polylactides Exhibit Degradability", *Tappi Journal*, Sep. 1991, p. 42. .

G. Van Hummel and S. Harkema ("Structure of 3,6–Dimethyl–1,4–Dioxane–2,5–Dione [D–,D–(L–,L–)Lactide]", 1982, *Acta. Crystallogr.*, v. B38, pp. 1679–1681).

F. Chabot, M. Vert, S. Chapelle and P. Granger ("Configurational Structures of Lactic Acid Stereocopolymers as Determined by $^{13}C(^{1}H)$ N.M.R.", 1983, *Polymer*, v. 24, pp. 53–59).

F. Kohn, J. Van Berg, G. VanDe Ridder and J. Feijen ("The Ring–Opening Polymerization of D,L–Lactide in the Melt Initiated with Tetraphenyltin", 1984, *Journal of Applied Polymer Science*, v. 29, pp. 4265–4277).

H. Kricheldorf and A. Serra ("Polylactones 6. Influence of Various Metal Salts on the Optical Purity of Poly(L–lactide)", 1985, *Polymer Bulletin.* v. 14, pp. 497–502).

A. Chawla and T. Chang ("In–Vivo Degradation of Poly-(lactic acid) of Different Molecular Weights", 1985, *Biomat., Med. Dev., Art. Org.,* v. 13, pp. 153–162).

I. McNeill and H. Leiper ("Degradation Studies of Some Polyesters and Polycarbones–1. Polylactide: Degradation Under Isothermal Conditions, Thermal Degradation Mechanism and Photolysis of the Polymer", 1985 *Polymer Degradation and Stability,* v. 11, pp. 309–326).

Makino et al. ("Preparation and in Vitro Degradation Properties of Polylactide Microcapsules", 1985, *Chem. Pharm. Bull.,* v. 33, pp. 1195–1201).

D. Garozzo, M. Giuffrida and G. Montaudo ("Primary Thermal Decomposition Processes in Aliphatic Polyesters Investigated by Chemical Ionization Mass Spectrometry", 1986, *Macromolecules,* v. 19, pp. 1643–1649).

"Irganos® 1076 Antioxidant and Thermal Stabilizer", (published on an unknown date in 1986 by Ciba–Geigy Corporation, Three Skyline Drive, Hawthorne, NY 10532).

J. Leenslag and A. Pennings ("Snythesis of High–molecular–weight–poly(L–lactide) initiated with tin 2–ethylhexanoate", 1987, *Makromol. Chem.,* v. 188, pp. 1809–1814).

Nakamura et al. ("Surgical Application of Biodegradable Films Prepared from Lactidee–Caprolactone Copolymers", 1987, *Bio. Materials and Clinical Applications,* v. 7, pp. 759–764).

H. Kricheldorf, M. Berl and N. Scharnagl ("Polymerization Mechanism of Metal Alkoxide Initiated Polymerizations Lactide and Various Lactones", 1988, *Makromol.,* v. 21, pp. 286–293).

K. Jamshidi, S. Hyon and Y. Ikada ("Thermal Characterization of Polylactides", 1988, *Polymer,* v. 29, pp. 2229–2234).

M. Vert (Bioresorbable Polymers for Temporary Therapeutic Applications, 1989, *Die angwandte Makromolekulare Chemie,* v. 166–167, pp. 155–168).

"Hydrolytic Stability/Corrosivity of Phosphite Costabilizers", (Technical Bulletin 89–04, published on an unknown date in 1989, by Stars Laboratory, Additives Division, Ciba–Geigy Corporation, Ardsley, NY 10502).

"GE Specialty Chemicals Product Guide CA–4001E", (published on an unknown date in 1989, by General Electric Company, 5th and Avery Street, Parkersburg, WV 26102).

"Tinuvin® 123 Hindered Aminoether Light Stabilizer for Coatings", (published on an unknown date in 1989, by Ciba–Geigy Corporation, Three Skyline Drive, Hawthorne, NY 10532).

"Irganoz® B–Blends Antioxidants and Process Stabilizers for Polymers", (published on an unknown date in Mar., 1990, by Ciba–Geigy Corporation, Three skyline Drive, Hawthorne, NY 10532).

"Naugard® 445, Specialty Chemicals", (a product brochure published on or before May 1, 1990, by Uniroyal Chemcial Company, Inc., Middlebury, CT 06749).

"Ethanox® 398 Antioxidant, The First Fluorophosphonite Antioxidant", (published on or before an unknown date in Oct., 1990, by Ethyl Corporation, 451 Florida Blvd., Baton Rouge, LA 70801).

"The Resomer® Resorbable Polyesters" (published on or before an unknown date in Feb., 1991 by Boehringer Ingelheim KG, D–6507 Ingelheim, W. Germany).

P. Kemchuk, ("Introduction to Polymer Degradation", lecture notes distributed at a seminar entitled: *Principles of Polymer Degradation and Stabilization* in Orlando, florida, Oct. 28–30, 1991, sponsored by The Institute of Materials Science, State University of New York at New Paltz).

R. Thomas, ("Degradation and Stabilization of Engineering Polymers", lecture notes distributed at a seminar entitled: *Principles of Polymer Degradation and Stabilization* in Orlando, Florida, Oct. 28–30, 1991, sponsored by The Institute of Materials Science, State University of New York at New Paltz).

W. Enlow, ("Process Stabilization with Phosphite Antioxidants", lecture notes distributed at a seminar entitled: *Principles of Polymer Degradation and Stabilization* in Orlando, Florida, Oct. 28–30, 1991,sponsored by The Institute of Materials Science, State University of New York at New Paltz).

"Naugard® XL–1 Specialty Chemicals", (product brochure published on an unknown date in Feb., 1992, by Uniroyal Chemical Co., Inc., Middlebury,CT 06749).

Sir John Meurig Thomas, ("Solid Acid Catalysts", Apr. 1992, *Scientific American,* pp. 112–118).

"Argus Product Data, Argus® Dimyristyl Thiodipropionate", (published on or before an unknown date in Aug., 1992, by Argus Division, Witco Corporation, 633 Court Street, Brooklyn, NY 11231–2193).

"Argus Thiochemical Product Data, Argus® Thiodipropionate", (published on or before an unknown date in Aug., 1992, by Argus Division, Witco Corporation, 633 Court Street, Brooklyn, NY 11231–2193).

"Argus Product Data, argus® Distearyl Thiodipropionate", (published on or before an unknown date in Aug., 1992, by argus Division, Witco Corporation, 633 Court Street, Brooklyn, NY 11231–2193).

"Argus Product Data, Mark® 2140 Pentaerythrityl Octythiopropionate", (published on or before an unknown date in Aug., 1992, by Argus Division, Witco Corporation, 633 Court Street, Brooklyn, NY 11231–2193).

"Argus Thiochemical Product Data, argus® Dilauryl Thiodipropionate" (published on or before an unknown date in Aug., 1992, by Argus Division, Witco Corporation, 633 Court Street, Brooklyn, NY 11231–2193).

"Argus Product Data, Seenox® 412S Pentaerythriotol Tetrakas (B–Laurylthiopropionat)", (published on or before an unknown date in Aug., 1992, by Argus Division, Witco Corporation, 633 Court Street, Brooklyn, NY 11231–2193).

"Irganox® 1010", (a product published on or before an unknown date in Aug., 1992, by Ciba–Geigy Corporation, Three Skyline Drive, Hawthorne, NY 10532).

"Irganoz® MD 1024, Metal Deactivator/Antioxidant", (published on an unknown date prior to Aug., 1992, by Ciba–Geigy Corporation, Three Skyline Drive, Hawthorne, NY 10532).

"Tinuvin® 622LD Low Dust, Hindered Amine Light Stabilizer for Polymers FDA–Cleared for Polyolefins", (published on an unknown date before Aug., 1992, by Ciba–Geigy Corporation, Three Skyline Drive, Hawthorne, NY 10532).

P.V. Bonsignore et al., 1992 Poly(lactic acid) Degradable Plastics, Coatings, and Binders, TAPPI Proceedings (Nonwovens Conference); pp. 129–140.

E.M. Filachione and C.H. Fisher, "Lactic acid condensation polymers, preparation by batch and continuous methods", *Industrial and Engineering Chemistry,* vol. 36, No. 3 (1944).

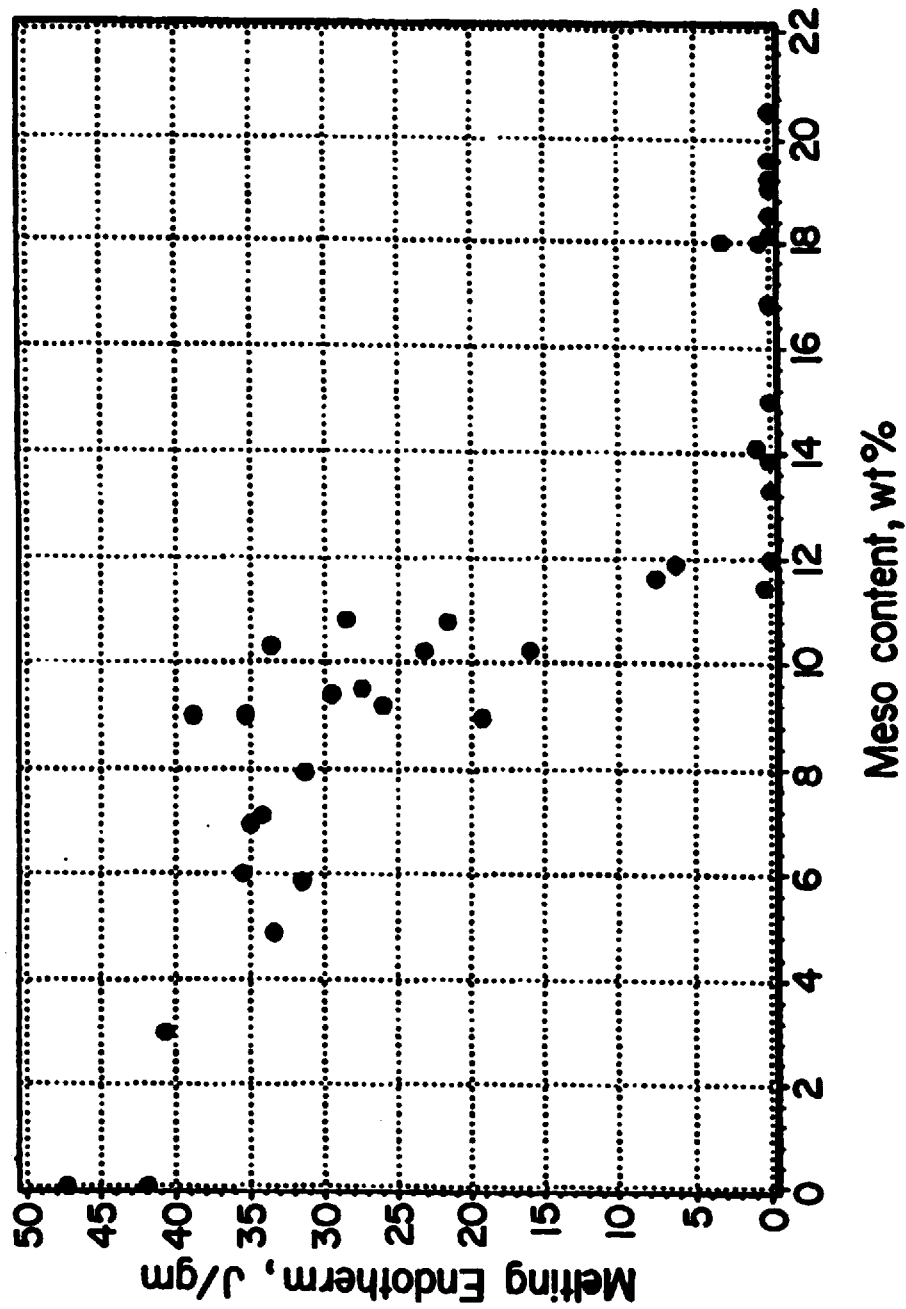

MELT-STABLE LACTIDE POLYMER NONWOVEN FABRIC AND PROCESS FOR MANUFACTURE THEREOF

CROSS REFERENCE TO RELATED APPLICATIONS

The present application is a continuing application of U.S. patent application Ser. No. 08/328,550 filed Oct. 25, 1994 and which has issued as U.S. Pat. No. 5,525,706 on Jun. 11, 1996. The parent application (Ser. No. 08/328,550) was a file-wrapper continuation of Ser. No. 08/071,590 filed Jun. 2, 1993 now abandoned which was a continuation-in-part of U.S. application Ser. No. 07/955,690 filed Oct. 2, 1992 and now U.S. Pat. No. 5,338,822. The parent application (Ser. No. 08/328,550) is incorporated herein by reference in its entirety.

BACKGROUND OF THE INVENTION

1. Field of the Invention

The present invention relates to a nonwoven fabric comprising a melt-stable, biodegradable lactide polymer composition and a process for manufacturing such nonwoven fabrics from a melt-stable, biodegradable lactide polymer.

2. Description of the Prior Art

The need for and uses of nonwoven fabrics have increased tremendously in recent years. Production of nonwoven roll goods was estimated at 2.5 billion pounds in 1992. Nonwoven fabrics are presently used for coverstock, interlinings, wipes, carrier sheets, furniture and bedding construction, filtration, apparel, insulation, oil cleanup products, cable insulating products, hospital drapes and gowns, battery separators, outerwear construction, diapers and feminine hygiene products.

There are basically three different manufacturing industries which make nonwovens; the textile, paper and extrusion industries. The textile industry garnets, cards or aerodynamically forms textile fibers into oriented webs. The paper industry employs technology for converting dry laid pulp and wet laid paper systems into nonwoven fabrics. The extrusion industry uses at least three methods of nonwoven manufacture, those being the spunbond, melt blown and porous film methods. The melt blown method involves extruding a thermoplastic resin through a needle thin die, exposing the extruded fiber to a jet of hot air and depositing the "blown" fiber on a conveyor belt. These fibers are randomly orientated to form a web. The spunbond method also utilizes a needle thin die, but orients or separates the fibers in some manner. The porous film method employs both slit and annular dies. In one method, a sheet is extruded and drawn, fibrillization occurs and a net-like fabric results.

A problem associated with current nonwoven materials is that recycling of the article containing the nonwoven fabric is generally not cost effective. In addition, disposal generally involves creating non-degradable waste. A vivid example is the disposal of diapers. Disposable diapers rely heavily on the use of nonwovens in their construction. Millions of diapers are disposed of each year. These disposable diapers end up in landfills or compost sites. The public is becoming increasingly alarmed over diapers that are not constructed of biodegradable material. In order to address the public's concern over the environment, diaper manufacturers are turning to biodegradable materials for use in their diapers. Currently, biodegradable materials made from starch based polymers, polycaprolactones, polyvinyl alcohols, and polyhydroxybutyrate-valerate-copolymers are under consideration for a variety of different uses in the disposable article market. However, to date, there has not been a satisfactory nonwoven fabric made from a biodegradable material which has properties that can withstand the present requirements of nonwoven fabrics.

Although not believed to be known as a precursor for nonwoven fabric, the use of lactic acid and lactide to manufacture a biodegradable polymer is known in the medical industry. As disclosed by Nieuwenhuis et al. (U.S. Pat. No. 5,053,485), such polymers have been used for making biodegradable sutures, clamps, bone plates and biologically active controlled release devices. Processes developed for the manufacture of polymers to be utilized in the medical industry have incorporated techniques which respond to the need for high purity and biocompatability in the final product. These processes were designed to produce small volumes of high dollar-value products, with less emphasis on manufacturing cost and yield.

In order to meet projected needs for biodegradable packaging materials, others have endeavored to optimize lactide polymer processing systems. Gruber et al. (U.S. Pat. No. 5,142,023) disclose a continuous process for the manufacture of lactide polymers with controlled optical purity from lactic acid having physical properties suitable for replacing present petrochemical-based polymers.

Generally, manufacturers of polymers utilizing processes such as those disclosed by Gruber et al. will convert raw material monomers into polymer beads, resins or other pelletized or powdered products. The polymer in this form may then be then sold to end users who convert, i.e., extrude, blow-mold, cast films, blow films, thermoform, injection-mold or fiber-spin the polymer at elevated temperatures to form useful articles. The above processes are collectively referred to as melt-processing. Polymers produced by processes such as those disclosed by Gruber et al., which are to be sold commercially as beads, resins, powders or other non-finished solid forms are generally referred to collectively as polymer resins.

Prior to the present invention, it is believed that there has been no disclosure of a combination of composition control and melt stability requirements which will lead to the production of commercially viable lactide polymer nonwoven fabrics.

It is generally known that lactide polymers or poly (lactide) are unstable. The concept of instability has both negative and positive aspects. A positive aspect is the biodegradation or other forms of degradation which occur when lactide polymers or articles manufactured from lactide polymers are discarded or composted after completing their useful life. A negative aspect of such instability is the degradation of lactide polymers during processing at elevated temperatures as, for example, during melt-processing by end-user purchasers of polymer resins. Thus, the same properties that make lactide polymers desirable as replacements for non-degradable petrochemical polymers also create undesirable effects during processing which must be overcome.

Lactide polymer degradation at elevated temperature has been the subject of several studies, including: I. C. McNeill and H. A. Leiper, *Polymer Degradation and Stability*, vol. 11, pp. 267–285 (1985); I. C. McNeil and H. A. Leiper, *Polymer Degradation and Stability*, vol. 11, pp. 309–326 (1985); M. C. Gupta and V. G. Deshmukh, *Colloid & Polymer Science*, vol. 260, pp. 308–311 (1982), M. C. Gupta and V. G. Deshmukh, *Colloid & Polymer Science*, vol. 260, pp. 514–517 (1982); Ingo Luderwald, *Dev. Polymer*

Degradation, vol. 2, pp. 77–98 (1979); Domenico Garozzo, Mario Giuffrida, and Giorgio Montaudo, *Macromolecules*, vol. 19, pp. 1643–1649 (1986); and, K. Jamshidi, S. H. Hyon and Y. Ikada, *Polymer*, vol. 29, pp. 2229–2234 (1988).

It is known that lactide polymers exhibit an equilibrium relationship with lactide as represented by the reaction below:

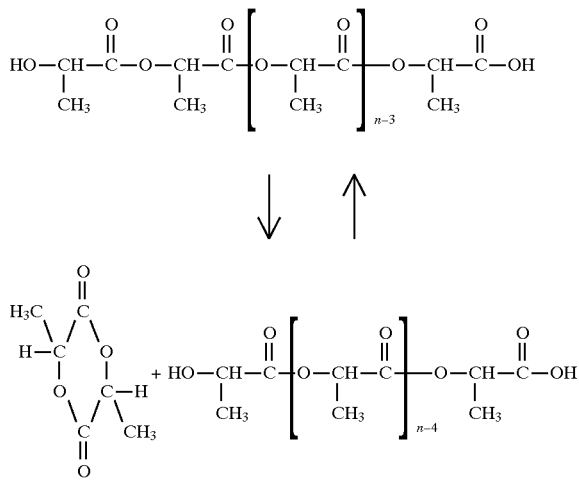

No consensus has been reached as to what the primary degradation pathways are at elevated processing temperatures. One of the proposed reaction pathways includes the reaction of a hydroxyl end group in a "back-biting" reaction to form lactide. This equilibrium reaction is illustrated above. Other proposed reaction pathways include: reaction of the hydroxyl end group in a "back-biting" reaction to form cyclic oligomers, chain scission through hydrolysis of the ester bonds, an intramolecular beta-elimination reaction producing a new acid end group and an unsaturated carbon-carbon bond, and radical chain decomposition reactions. Regardless of the mechanism or mechanisms involved, the fact that substantial degradation occurs at elevated temperatures, such as those used by melt-processors, creates an obstacle to use of lactide polymers as a replacement for petrochemical-based polymers. It is apparent that degradation of the polymer during melt-processing must be reduced to a commercially acceptable rate while the polymer maintains the qualities of biodegradation or compostability which make it so desirable. It is believed this problem has not been addressed prior to the developments disclosed herein.

As indicated above, poly(lactide)s have been produced in the past, but primarily for use in medical devices. These polymers exhibit biodegradability, but also a more stringent requirement of being bioresorbable or biocompatible. As disclosed by M. Vert, *Die Ingwandte Makromolekulare Chemie*, vol. 166–167, pp. 155–168 (1989), "The use of additives is precluded because they can leach out easily in body fluids and then be recognized as toxic, or, at least, they can be the source of fast aging with loss of the properties which motivated their use. Therefore, it is much more suitable to achieve property adjustment through chemical or physical structure factors, even if aging is still a problem." Thus, work aimed at the bioresorbable or biocompatible market focused on poly(lactide) and blends which did not include any additives.

Other disclosures in the medical area include Nieuwenhuis (European Patent No. 0 314 245), Nieuwenhuis (U.S. Pat. No. 5,053,485), Eitenmuller (U.S. Pat. No. 5,108,399), Shinoda (U.S. Pat. No. 5,041,529), Fouty (Canadian Patent No. 808,731), Fouty (Canadian Patent No. 923,245), Schneider (Canadian Patent No. 863,673), and Nakamura et al., *Bio. Materials and Clinical Applications*, Vol. 7, p. 759 (1987). As disclosed in these references, in the high value, low volume medical specialty market, poly(lactide) or lactide polymers and copolymers can be given the required physical properties by generating lactide of very high purity by means of such methods as solvent extraction or recrystallization followed by polymerization. The polymer generated from this high purity lactide is a very high molecular weight product which will retain its physical properties even if substantial degradation occurs and the molecular weight drops significantly during processing. Also, the polymer may be precipitated from a solvent in order to remove residual monomer and catalysts. Each of these treatments add stability to the polymer, but clearly at a high cost which would not be feasible for lactide polymer compositions which are to be used to replace inexpensive petrochemical-based polymers in the manufacture of nonwoven products.

Furthermore, it is well-known that an increase in molecular weight generally results in an increase in a polymer's viscosity. A viscosity which is too high can prevent melt-processing of the polymer due to physical/mechanical limitations of the melt-processing equipment. Melt-processing of higher molecular weight polymers generally requires the use of increased temperatures to sufficiently reduce viscosity so that processing can proceed. However, there is an upper limit to temperatures used during processing. Increased temperatures increase degradation of the lactide polymer, as the previously-cited studies disclose.

Jamshidi et al., *Polymer*, Vol. 29, pp. 2229–2234 (1988) disclose that the glass transition temperature of a lactide polymer, $T_g$, plateaus at about 57° C. for poly(lactide) having a number average molecular weight of greater than 10,000. It is also disclosed that the melting point, $T_m$, of poly (L-lactide) levels off at about 184° C. for semicrystalline lactide polymers having a number average molecular weight of about 70,000 or higher. This indicates that at a relatively low molecular weight, at least some physical properties of lactide polymers plateau and remain constant.

Sinclair et al. (U.S. Pat. No. 5,180,765) disclose the use of residual monomer, lactic acid or lactic acid oligomers to plasticize poly(lactide) polymers, with plasticizer levels of 2–60 percent. Loomis (U.S. Pat. No. 5,076,983) discloses a process for manufacturing a self-supporting film in which the oligomers of hydroxy acids are used as plasticizing agents. Loomis and Sinclair et al. disclose that the use of a plasticizer such as lactide or lactic acid is beneficial to produce more flexible materials which are considered to be preferable. Sinclair et al., however, disclose that residual monomer can deposit out on rollers during processing. Loomis also recognizes that excessive levels of plasticizer can cause unevenness in films and may separate and stick to and foul processing equipment. Thus, plasticizing as recommended, negatively impacts melt-processability in certain applications.

Accordingly, a need exists for a lactide polymer composition which is melt-stable under the elevated temperatures common to melt-processing resins in the manufacture of nonwoven fabrics. The needed melt-stable polymer composition must also exhibit sufficient compostability or degradability after its useful life as a nonwoven fabric. Further, the melt-stable polymer must be processable in existing melt-processing equipment, by exhibiting sufficiently low viscosities at melt-processing temperatures while polymer degradation and lactide formation remains below a point of substantial degradation and does not cause excessive fouling of processing equipment. Furthermore, the polymer lactide must retain its molecular weight, viscosity and other physical properties within commercially-acceptable levels through the nonwoven manufacturing process. It will be further appreciated that a need also exists for a process for manufacturing such nonwoven fabrics. The present invention addresses these needs as well as other problems associated with existing lactide polymer compositions and manufacturing processes. The present invention also offers further advantages over the prior art, and solves other problems associated therewith.

SUMMARY OF THE INVENTION

According to the present invention, a nonwoven fabric comprising a plurality of fibers is provided. A first portion of the plurality of fibers comprise a melt-stable lactide polymer composition comprising: a plurality of poly(lactide) polymer chains having a number average molecular weight of from about 10,000 to about 300,000; lactide in a concentration of less than about 2 percent by weight; and water in a concentration of less than about 2,000 parts per million. A process for the manufacture of the nonwoven fabric is also provided. For the purposes of the present invention, the nonwoven fabric may be manufactured from any number of methods and is not to be limited by the particular method.

Optionally, stabilizing agents in the form of anti-oxidants and water scavengers may be added. Further, plasticizers, nucleating agents and/or anti-blocking agents may be added. The resultant nonwoven fabric is biodegradable and may be disposed of in an environmentally sound fashion.

Poly(lactide) is a polymeric material which offers unique advantages as a fiber for nonwovens not only in the biodegradable sense, but in the manufacturing process as well.

Poly(lactide) offers advantages in the formation of the nonwoven fabric in a melt extrusion process. One problem that is sometimes encountered in the extrusion of fibers into a nonwoven web is poor adhesion of the fibers to one another upon cooling. Two characteristics of poly(lactides) lend themselves to enhanced adhesion low viscosity and high polarity. Mechanical adhesion, the interlocking of fibers at adjoining points, increases as the viscosity decreases. An advantage of poly(lactide) is that the viscosity lends itself well to fiber formation. Thus, poly(lactide) fibers adhere to one another well, resulting in a web with added strength. Also, because the surface is typically polar for most fibers, the high polarity of the poly(lactide) offers many dipole-dipole interactions, further resulting in enhanced adhesion In melt blown processes, the fibers of the present invention have small diameters which are beneficial for many applications. The present fibers can have diameters of less than about 5 $\mu$m.

The fibers of the nonwoven web of the present invention are superior to typical polypropylene nonwoven webs in diaper construction. The typical construction of a diaper comprises an outer, water impervious back sheet, a middle, absorbent layer and an inner layer, which is in contact with the diaper wearer. The inner layer is typically made from a soft, nonwoven material such as a polypropylene nonwoven web. However, polypropylene, due to its low polarity, has to be surface modified such that the urine passes through the inner layer, rather than being repelled. A significant advantage of the present invention is that the polarity of the poly(lactide) (without surface treatment) is ideally suited such that urine readily passes through the nonwoven web, but is not absorbed by the layer. Thus, the poly(lactide) web of the present invention also may superior inner layer for diaper construction. The present invention may also be employed in incontinent and feminine hygiene products.

The nonwoven fabric of the present invention also may be used in packaging and bagging operations. Food packaging which does not require water tight packaging but requires breathability is an example of a use of the present invention. Bags such as leaf or yard bags may also be made from the nonwoven fabric of the present invention. The fabric is porous to allow air to enter the bag to begin decomposing the leaves. This is advantageous over present leaf bags, which do not allow air to penetrate into the leaf cavity. Further, the present nonwoven fabric, when used as a leaf bag, decomposes along with the leaves, thus minimizing the adverse environmental impact of the leaf bags.

Poly(lactide) processes at lower temperatures which allows the fiber to be extruded at lower temperatures than traditional polymers. This results in a cost savings to the converter because the extrusion equipment will not require as much power when run at lower temperatures. There is also increased safety associated with lower temperatures.

A significant advantage of poly(lactide) over many nonwoven fabrics used today such as polypropylene is its biodegradability. The continued depletion of landfill space and the problems associated with incineration of waste have led to the need for development of a truly biodegradable nonwoven fabric to be utilized as a substitute for non-biodegradable or partially biodegradable petrochemical-based nonwoven fabrics. Furthermore, a poly(lactide) nonwoven web, unlike other biodegradable polymers, is believed to not support microbial growth. Starch or other biodegradable polymers, when exposed to warm, damp environments, will promote the growth of unhealthy microbes. This is undesirable in the diaper industry. Thus the present invention has yet another advantage over prior biodegradable polymers.

The above described features and advantages along with various other advantages and features of novelty are pointed out with particularity in the claims of the present application. However, for a better understanding of the invention, its advantages, and objects attained by its use, reference should be made to the drawings which form a further part of the present application and to the accompanying descriptive matter in which there is illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views;

FIG. 3 is a graph showing the relationship between meso-lactide concentration and energy of melting.

DETAILED DESCRIPTION OF THE PREFERRED EMBODIMENT(S)

Figure 1:
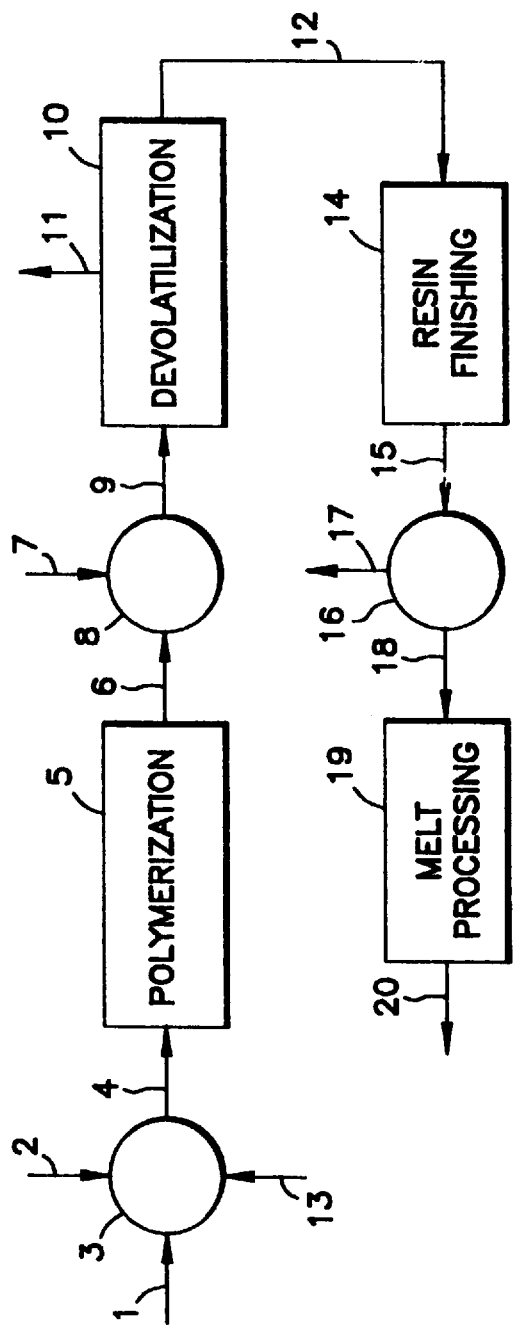
FIG. 1 is a schematic representation of a preferred process for the manufacture of a melt-stable lactide polymer composition.

The lactide polymer compositions used in nonwoven fabrics disclosed herein focus on meeting the requirements of the end user melt-processor of a lactide polymer resin such as that produced from a process disclosed by Gruber et al. However, the present invention is directed to a poly (lactide) fiber and is not limited to the lactide polymer composition or process of Gruber et al. Any lactide polymer composition, which comes within the scope of this invention, may be used as a fiber for a nonwoven fabric. As disclosed herein, the problems of degradation, fouling, and lactide formation during melt-processing of lactide polymers are addressed through suggested ranges of molecular weights and compositional limits on impurities such as residual monomer, water and catalyst along with the use of stabilizing agents and catalyst-deactivating agents.

In general, according to the present invention, a melt-stable lactide polymer nonwoven fabric and a process for manufacturing a melt-stable lactide polymer nonwoven fabric from a melt-stable lactide polymer are disclosed. Lactide polymers are useful due to their biodegradable nature. Furthermore, lactide polymers are compostable as illustrated in Example 15 below. Applicants believe the hydrolysis of the ester may be the key to or the first step in degradation of a lactide polymer composition. The mechanism of degradation is not key to the nonwoven fabric of the present invention, however it must be recognized that such degradation makes lactide polymers desirable as replacements for presently-utilized non-degradable petrochemical-based polymers used for nonwovens.

Applicants have found that the instability of lactide polymers which leads to the beneficial degradation discussed above also creates processing problems. These processing problems include generation of lactide monomer at elevated temperatures and loss in molecular weight believed due to chain scission degradation of the ester bonds and other depolymerization reactions which are not completely understood. No consensus has been reached as to what are the primary degradation pathways at elevated processing temperatures. As previously disclosed, these may include such pathways as equilibrium-driven depolymerization of lactide polymers to form lactide and chain scission through hydrolysis of the ester bonds along with other pathways. For purposes of the present invention, the exact mechanism of degradation at elevated temperatures is not critical.

It is to be understood, however, that degradation of lactide polymers is both beneficial and detrimental. Benefits derive from degradability when articles manufactured from such polymers are discarded. The same or similar types of degradation are detrimental if they occur during processing or prior to the end of the article's useful life.

Melt-Processing

It is believed that a manufacturer of lactide polymers from a lactide monomer will produce a lactide polymer resin which is in the form of beads or pellets. The melt-processor will convert the resin to a fiber for a nonwoven fabric by elevating the temperature of the resin above at least its glass transition temperature but normally higher and extruding the fiber into a nonwoven fabric. It is to be understood that the conditions of elevated temperature used in melt-processing cause degradation of lactide polymers during processing. Degradation under melt-processing conditions is shown experimentally in Example 7 based on equilibrium, Example 10 based on catalyst concentration, Example 11 based on catalyst activity, Example 13 based on use of stabilizers and Example 14 based on moisture content. As can be seen in these examples, it is understood that several factors appear to affect the rate of degradation during melt-processing. Applicants have addressed these factors in a combination of compositional requirements and the addition of stabilizing or catalyst-deactivating agents to result in a polymer of lactide which is melt-stable.

In addition, melt-processing frequently produces some proportion of trimmed or rejected material. Environmental concerns and economical efficiencies dictate that this material be reused, typically by regrinding and adding back the material into the polymer feed. This introduces additional thermal stress on the polymer and increases the need for a melt-stable polymer composition.

Melt Stability

The lactide polymers of the present invention are melt-stable. By "melt-stable" it is meant generally that the lactide polymer, when subjected to melt-processing techniques, adequately maintains its physical properties and does not generate by-products in sufficient quantity to foul or coat processing equipment. The melt-stable lactide polymer exhibits reduced degradation and/or reduced lactide formation relative to known lactide polymers. It is to be understood that degradation will occur during melt-processing. The compositional requirements and use of stabilizing agents as disclosed herein reduces the degree of such degradation to a point where physical properties are not significantly affected by melt-processing and fouling by impurities or degradation by-products such as lactide does not occur. Furthermore, the melt-stable polymer should be melt-processable in melt-processing equipment such as that available commercially. Further, the polymer will preferably retain adequate molecular weight and viscosity. The polymer should preferably have sufficiently low viscosity at the temperature of melt-processing so that the extrusion equipment may create an acceptable nonwoven fabric. The temperature at which this viscosity is sufficiently low will preferably also be below a temperature at which substantial degradation occurs.

Polymer Composition

The melt-stable lactide polymer nonwoven fabric of the present invention comprises a plurality of poly(lactide) polymer chains having a number average molecular weight from about 10,000 to about 300,000. In a preferred composition for a melt blown nonwoven, the number average molecular weight ranges from about 15,000 to about 100,000. In the most preferred composition, the number average molecular weight ranges from about 20,000 to about 80,000. In a spunbond nonwoven fabric, the preferred number average molecular weight range is from about 50,000 to about 250,000. In a most preferred embodiment, the number average molecular weight range is from about 75,000 to about 200,000.

As detailed in Example 9, it appears that the physical properties such as modulus, tensile strength, percentage elongation at break, impact strength, flexural modulus, and flexural strength remain statistically constant when the lactide polymer samples are above a threshold molecular weight. The lower limit of molecular weight of the polymer compositions of the present invention is set at a point above the threshold of which a fiber has sufficient diameter and density. In other words, the molecular weight cannot be lower than is necessary to achieve a targeted fiber diameter and density. As detailed in Example 22, there is a practical upper limit on molecular weight based on increased viscosity with increased molecular weight. In order to melt-process a high molecular weight lactide polymer, the melt-processing temperature must be increased to reduce the viscosity of the polymer. As pointed out in the Examples, the exact upper limit on molecular weight must be determined for each melt-processing application in that required viscosities vary and residence time within the melt-processing equipment will also vary. Thus, the degree of degradation in each type of processing system will also vary. Based on the disclosure of Example 22, it is believed that one could determine the suitable molecular weight upper limit for meeting the viscosity and degradation requirements in any application.

Lactide polymers can be in either an essentially amorphous form or in a semi-crystalline form. For various applications it will be desirable to have the polymer in one of these configurations. As detailed in Example 24, the desired range of compositions for semi-crystalline poly (lactide) is less than about 12 percent by weight meso-lactide and the remaining percent by weight either L-lactide or D-lactide, with L-lactide being more readily available. A more preferred composition contains less than about 9 percent by weight meso-lactide with the remainder being substantially all L-lactide.

For applications where an amorphous polymer is desired, the preferred composition of the reaction mixture is above 9 percent by weight meso-lactide and a more preferred composition contains above 12 percent by weight meso-lactide lactide with the remaining lactide being substantially all L-lactide mixture, or D-lactide can be used to control the potential crystallinity in a predominantly L-lactide mixture.

Addition of even small amounts of meso-lactide to the polymerization mixture results in a polymer which is even slower to crystallize than polymerization mixtures having lesser amounts of meso-lactide, as detailed in Example 23. Beyond about 12% meso content the polymer remains essentially amorphous following a typical annealing procedure. This contrasts with the behavior of D,L-lactide, which can be added at a concentration of 20 percent to the polymerization mixture and still produce a semi-crystalline polymer following the annealing procedure. These results are detailed in Example 24.

There are three main methods to increase the rate of crystallization. One is to increase chain mobility at low temperatures, by adding for example, a plasticizing agent. The plasticizer must be selected carefully, however, and preferably will be of limited compatibility so that it will migrate to the amorphous phase during crystallization. Dioctyl adipate is an example of a plasticizer which helps crystallization rates in poly(lactide), as detailed in Example 25. A second method to increase the rate of crystallization is to add a nucleating agent, as detailed in Example 26. A third method is to orient the polymer molecules. Orientation can be accomplished by drawing during film casting, drawing of fibers, blowing films, stretching of film or sheet after it is cast (in multiple directions, if desired), or by the flow of polymer through a small opening in a die. The alignment generated helps to increase the rate of crystallization, as detailed in Example 27.

Heat setting may also be employed to increase the degree of crystallinity in the fibers. Heat setting involves exposing the fabric to elevated temperatures, as shown in Plastics Extrusion Technology, F. Hensen (ed), Hanser Publishers, New York, 1988, pp 308, 324. It is preferred to heat set with the fiber or nonwoven fabric under tension to reduce shrinkage during the setting process.

Applicants recognize that an essentially amorphous lactide polymer may have some crystallinity. Crystalline poly L-lactide exhibits an endotherm of roughly 92 Joules per gram at its melting temperature of 170°–190° C. The melting point changes with composition. The degree of crystallinity is roughly proportional to the endotherm on melting. For purposes of the present invention, it is meant by an amorphous or non-crystalline poly(lactide) to be a poly(lactide) or lactide polymer which exhibits a melting endotherm of less than about 10 Joules per gram in the temperature range of about 130°–200° C. Semi-crystalline poly(lactide) exhibits a melting endotherm above about 10 joules per gram.

The residual monomer concentration in the melt-stable lactide polymer composition is less than about 2 percent by weight. In a preferred composition, the lactide concentration is less than about 1 percent by weight, and a most preferred composition has less than about 0.5 percent by weight of lactide. Contrary to disclosures in the art, Applicants have found that the monomer cannot be used as a plasticizing agent in the resin of the present invention due to significant fouling of the extrusion equipment. As detailed in Example 16, it is believed the low levels of monomer concentration do not plasticize the final polymer.

The water concentration within the melt-stable lactide polymer composition is less than about 2,000 parts-per-million. Preferably this concentration is less than 500 parts-per-million and most preferably less than about 100 parts-per-million. As detailed in Example 14, the polymer melt-stability is significantly affected by moisture content. Thus, the melt-stable polymer of the present invention must have the water removed prior to melt processing. Applicants recognize that water concentration may be reduced prior to processing the polymerized lactide to a resin. Thus, moisture control could be accomplished by packaging such resins in a manner which prevents moisture from contacting the already-dry resin. Alternatively, the moisture content may be reduced at the melt-processor's facility just prior to the melt-processing step in a dryer. Example 14 details the benefit of drying just prior to melt-processing and also details the problems encountered due to water uptake in a polymer resin if not stored in a manner in which moisture exposure is prevented or if not dried prior to melt-processing. As detailed in these examples, Applicants have found that the presence of water causes excessive loss of molecular weight which may affect the physical properties of the melt-processed polymer.

In a preferred composition of the present invention, a stabilizing agent is included in the polymer formulation to reduce degradation of the polymer during production devolatilization, drying and melt processing by the end user. The stabilizing agents recognized as useful in the present nonwoven fibers may include antioxidants and/or water scavengers. Preferred antioxidants are phosphite-containing compounds, hindered phenolic compounds or other phenolic compounds. The antioxidants include such compounds as trialkyl phosphites, mixed alkyl/aryl phosphites, alkylated aryl phosphites, sterically hindered aryl phosphites, aliphatic spirocyclic phosphites, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones and mixtures thereof. As detailed in Example 13, many commercially-available stabilizing agents have been tested and fall within the scope of the present melt-stable lactide polymer nonwoven fabric composition. Biodegradable antioxidants are particularly preferred.

The water scavengers which may be utilized in preferred embodiments of the melt-stable lactide polymer nonwoven fiber include: carbodiimides, anhydrides, acyl chlorides, isocyanates, alkoxy silanes, and desiccant materials such as clay, alumina, silica gel, zeolites, calcium chloride, calcium carbonate, sodium sulfate, bicarbonates or any other compound which ties up water. Preferably the water scavenger is degradable or compostable. Example 19 details the benefits of utilizing a water scavenger.

In a preferred composition of the present invention, a plasticizer is included in the polymer formulation to improve the nonwoven fiber quality of the lactide polymer. More particularly, plasticizers reduce the melt viscosity at a given temperature of poly(lactide), which aides in processing and extruding the polymer at lower temperatures and may improve flexibility and reduce cracking tendencies of the finished fabric. Plasticizers also lower the melt viscosity of poly(lactide), thereby making it easier to draw-down the fibers to a small diameter.

A plasticizer is useful in concentration levels of about 1 to 35 percent. Preferably, a plasticizer is added at a concentration level of about 5 to 25 percent. Most preferably, a plasticizer is added at a concentration level of about 8 to 25 percent.

Selection of a plasticizing agent requires screening of many potential compounds and consideration of several criteria. For use in a biodegradable nonwoven fabric the preferred plasticizer is to be biodegradable, non-toxic and compatible with the resin and relatively nonvolatile.

Plasticizers in the general classes of alkyl or aliphatic esters, ether, and multi-functional esters and/or ethers are preferred. These include alkyl phosphate esters, dialkylether diesters, tricarboxylic esters, epoxidized oils and esters, polyesters, polyglycol diesters, alkyl alkylether diesters, aliphatic diesters, alkylether monoesters, citrate esters, dicarboxylic esters, vegetable oils and their derivatives, and esters of glycerine. Most preferred plasticizers are tricarboxylic esters, citrate esters, esters of glycerine and dicarboxylic esters. Citroflex A4® from Morflex is particularly useful. These esters are anticipated to be biodegradable. Plasticizers containing aromatic functionality or halogens are not preferred because of their possible negative impact on the environment.

For example, appropriate non-toxic character is exhibited by triethyl citrate, acetyltriethyl citrate, tri-n-butyl citrate, acetyltri-n-butyl citrate, acetyltri-n-hexyl citrate, n-butyltri-n-hexyl citrate and dioctyl adipate. Appropriate compatibility is exhibited by acetyltri-n-butyl citrate and dioctyl adipate. Other compatible plasticizers include any plasticizers or combination of plasticizers which can be blended with poly(lactide) and are either miscible with poly(lactide) or which form a mechanically stable blend. Corn oil and mineral oil were found to be incompatible when used alone with poly(lactide) because of phase separation (not mechanically stable) and migration of the plasticizer.

Volatility is determined by the vapor pressure of the plasticizer. An appropriate plasticizer must be sufficiently non-volatile such that the plasticizer stays substantially in the resin formulation throughout the process needed to produce the nonwoven fabric. Excessive volatility can lead to fouling of process equipment, which is observed when producing fabrics by melt processing poly(lactide) with a high lactide content. Preferred plasticizers should have a vapor pressure of less than about 10 mm Hg at 170° C., more preferred plasticizers should have a vapor pressure of less than 10 mm Hg at 200° C. Lactide, which is not a preferred plasticizer, has a vapor pressure of about 40 mm Hg at 170° C. Example 6 highlights useful plasticizers for the present invention.

In a preferred composition, nucleating agents may be incorporated during polymerization. Nucleating agents may include selected plasticizers, finely divided minerals, organic compounds, salts of organic acids and imides and finely divided crystalline polymers with a melting point above the processing temperature of poly(lactide). Examples of useful nucleating agents include talc, sodium salt of saccharin, calcium silicate, sodium benzoate, calcium titanate, boron nitride, copper phthalocyanine, isotactic polypropylene, low molecular weight poly(lactide) and polybutylene terephthalate, In a preferred composition, fillers may be useful to prevent blocking or sticking of layers or rolls of the non-woven fabric during storage and transport. Inorganic fillers include clays and minerals, either surface modified or not. Examples include talc, diatomaceous earth, silica, mica, kaolin, titanium dioxide, and wollastonite. Preferred inorganic fillers are environmentally stable and non-toxic.

Organic fillers include a variety of forest and agricultural products, either with or without modification. Examples include cellulose, wheat, starch, modified starch, chitin, chitosan, keratin, cellulosic materials derived from agricultural products, gluten, nut shell flour, wood flour, corn cob flour, and guar gum. Preferred organic fillers are derived from renewable sources and are biodegradable. Fillers may be used either alone or as mixtures of two or more fillers. Example 5 highlights useful anti-blocking fillers for the present invention.

Surface treatments may also be used to reduce blocking. Such treatments include corona and flame treatments which reduce the surface contact between the poly(lactide) based fabric and the adjacent surface.

For certain applications, it is desirable for the fabric to be modified to alter the water transport properties. Surfactants may be incorporated into the web of the present invention to increase the water transport properties.

Surfactants which are useful can be subdivided into cationic, anionic, and nonionic agents.

With regard to cationic compounds, the active molecule part generally consists of a voluminous cation which often contains a long alkyl residue (e.g. a quaternary ammonium, phosphonium or sulfonium salt) whereby the quaternary group can also occur in a ring system (e.g. imidazoline). In most cases, the anion is the chloride, methosulfate or nitrate originating from the quaternization process.

In the anionic compounds, the active molecule part in this class of compounds is the anion, mostly an alkyl sulfonate, sulfate or phosphate, a dithiocarbamate or carboxylate. Alkali metals often serve as cations.

Nonionic antistatic agents are uncharged surface-active molecules of a significantly lower polarity than the above mentioned ionic compounds and include polyethylene glycol esters or ethers, fatty acid esters or ethanolamides, mono- or diglycerides or ethyoxylated fatty amines. The above surfactants may also act as antistatic agents, which may be desirable.

Pigments or color events may also be added as necessary. Examples include titanium dioxide, clays, calcium carbonate, talc, mica, silica, silicates, iron oxides and hydroxide, carbon black and magnesium oxide.

In the manufacture of the melt-stable lactide polymer compositions of the present invention, the reaction to polymerize lactide is catalyzed. Many catalysts have been cited in literature for use in the ring-opening polymerization of lactones. These include but are not limited to: $SnCl_2, SnBr_2$, $SnCl_4$, $SnBr_4$, aluminum alkoxides, tin alkoxides, zinc alkoxides, SnO, PbO, Sn (2-ethyl hexanoates), Sb (2-ethyl hexanoates), Bi (2-ethyl hexanoates), Na (2-ethyl hexanoates) (sometimes called octoates), Ca stearates, Mg stearates, Zn stearates, and tetraphenyltin. Applicants have also tested several catalysts for polymerization of lactide at 180° C. which include: tin(II) bis(2-ethyl hexanoate) (commercially available from Atochem, as Fascat 2003, and Air Products as DABCO T-9), dibutyltin diacetate (Fascat 4200®, Atochem), butyltin tris(2-ethyl hexanoate) (Fascat 9102®, Atochem), hydrated monobutyltin oxide (Fascat 9100®, Atochem), antimony triacetate (S-21, Atochem), and antimony tris(ethylene glycoxide) (S-24, Atochem). Of these catalysts, tin(II) bis-(2-ethyl hexanoate), butyltin tris (2-ethyl hexanoate) and (butyltin diacetate appear to be most effective.

Applicants have found the use of catalysts to polymerize lactide significantly affects the stability of the resin product. It appears the catalyst as incorporated into the polymer also is effective at catalyzing the reverse depolymerizations reaction. Example 10 details the effect of residual catalyst on degradation. To minimize this negative effect, in a preferred composition, the residual catalyst level in the resin is present in a molar ratio of initial monomer-to-catalyst greater than about 3,000:1, preferably greater than about 5,000:1 and most preferably greater than about 10,000:1. Applicants believe a ratio of about 20,000:1 may be used, but polymerization will be slow. Optimization of catalyst levels and the benefits associated therewith are detailed in Example 20. Applicants have found that when the catalyst level is controlled within these parameters, catalytic activity is sufficient to polymerize the lactide while sufficiently low to enable melt-processing without adverse effect when coupled with low residual monomer level and low water concentration as described above in polymers of molecular weight between 10,000 to about 300,000. It is believed in most applications the addition of a stabilizing agent may be unnecessary if catalyst level is optimized.

Applicants have also found that catalyst concentration may be reduced subsequent to polymerization by precipitation from a solvent. Example 21 demonstrates potential catalyst removal by precipitation from a solvent. This produces a resin with reduced catalyst concentration. In an alternative embodiment, the catalyst means for catalyzing the polymerization of lactide to form the poly(lactide) polymer chains which was incorporated into the melt-stable lactide polymer composition during polymerization is deactivated by including in the melt-stable lactide polymer composition a catalyst deactivating agent in amounts sufficient to reduce catalytic depolymerization of the poly (lactide) polymer chains. Example 11 details the benefits of utilizing a catalyst deactivating agent. Such catalyst-deactivating agents include hindered, alkyl, aryl and phenolic hydrazides, amides of aliphatic and aromatic mono- and dicarboxylic acids, cyclic amides, hydrazones and bishydrazones of aliphatic and aromatic aldehydes, hydrazides of aliphatic and aromatic mono- and dicarboxylic acids, bis-acylated hydrazine derivatives, and heterocyclic compounds. A preferred metal deactivator is Irganox® MD1024 from Ciba-Geigy. Biodegradable metal deactivators are particularly preferred.

In an alternative embodiment, the catalyst concentration is reduced to near zero by utilizing a solid-supported catalyst to polymerize lactide. The feasibility of utilizing such a catalyst is detailed in Example 8. It is believed catalysts which may be utilized include supported metal catalysts, solid acid catalysts, acid clays, alumina silicates, alumina, silica and mixtures thereof.

In a preferred composition, the catalyst usage and/or deactivation is controlled to reduce depolymerization of the poly(lactide) polymer during melt-processing to less than about 2 percent by weight generation of lactide from a devolatilized sample in the first hour at 180° and atmospheric pressure. More preferably, the amount of lactide generated is less than about 1 percent by weight in the first hour and most preferably less than about 0.5 percent by weight in the first hour.

A preferred melt-stable lactide polymer composition is the reaction product of polymerization of lactide at a temperature greater than about 160° C. Applicants have found that polymerization at higher temperatures result in a characteristically different polymer which is believed to have improved melt stability due to increased transesterification during polymerization. The benefits of higher temperature polymerization are detailed in Example 12.

Melt-Stable Lactide Polymer Process

The process for the manufacture of a melt-stable lactide polymer comprises the steps of first providing a lactide mixture wherein the mixture contains about 0.5 percent by weight to about 50 percent by weight meso-lactide and about 99.5 percent by weight or less L-lactide and/or D-lactide. Such purified lactide stream may be such as that produced in the process disclosed by Gruber et al., although the source of lactide is not critical to the present invention.

The lactide mixture is polymerized to form a lactide polymer or poly(lactide) with some residual unreacted monomer in the presence of a catalyst means for catalyzing the polymerization of lactide to form poly(lactide). Catalysts suitable for such polymerization have been listed previously. The concentration of catalysts utilized may be optimized as detailed in the following examples and discussed previously.

In a preferred embodiment, a stabilizing agent, which may be an antioxidant and/or a water scavenger is added to the lactide polymer. It is recognized that such stabilizing agents may be added simultaneously with or prior to the polymerization of the lactide to form the lactide polymer. The stabilizing agent may also be added subsequent to polymerization.

As previously disclosed, the catalyst usage is adjusted and/or deactivation agent is added in a sufficient amount to reduce depolymerization of poly(lactide) during melt-processing to less than 2 percent by weight generation of lactide from a devolatilized sample in the first hour at 180° C. and atmospheric pressure. More preferably, the stabilizing agent controls lactide generation to less than 1 percent by weight and most preferably less than 0.5 percent by weight in the first hour at 180° C. and atmospheric pressure. Alternatively, the control of catalyst concentration to optimize the balance between necessary catalytic activity to produce poly(lactide) versus the detrimental effects of catalytic depolymerization or degradation of the lactide polymer may be utilized to obviate the need for adding a stabilizing agent.

The lactide polymer is then devolatilized to remove unreacted monomer which may also be a by-product of decomposition reactions or the equilibrium-driven depolymerization of poly(lactide). Any residual water which may be present in the polymer would also be removed during devolatilization, although it is recognized that a separate drying step may be utilized to reduce the water concentration to less than about 2,000 parts-per-million. The devolatilization of the lactide polymer may take place in any known devolatilization process. The key to selection of a process is operation at an elevated temperature and usually under conditions of vacuum to allow separation of the volatile components from the polymer. Such processes include a stirred tank devolatilization or a melt-extrusion process which includes a devolatilization chamber and the like An inert gas sweep is useful for improved devolatilization.

In a preferred process for manufacture of a melt-stable lactide polymer composition, the process also includes the step of adding a molecular weight control agent to the lactide prior to catalyzing the polymerization of the lactide. For examples molecular weight control agents include active hydrogen-bearing compounds, such as lactic acid, esters of lactic acid, alcohols, amines, glycols, diols and triols which function as chain-initiating agents. Such molecular weight control agents are added in sufficient quantity to control the number average molecular weight of the poly(lactide) to between about 10,000 and about 300,000.

Next referring to FIG. 1 which illustrates a preferred process for producing a melt-stable lactide polymer composition. A mixture of lactides enters a mixing vessel (3) through a pipeline (1). A catalyst for polymerizing lactide is also added through a pipeline (13). Within mixing vessel (3) a stabilizing agent may be added through a pipeline (2). A water scavenger may also be added through the pipeline (2). The stabilized lactide mixture is fed through a pipeline (4) to a polymerization process (5). The polymerized lactide or lactide polymer leaves the polymerization process through a pipeline (6). The stream is fed to a second mixing vessel (8) within which a stabilizing agent and/or catalyst deactivating agent may be added through a pipeline (7). The stabilized lactide polymer composition is then fed to a devolatilization process (10) through a pipeline (9) Volatile components leave the devolatilization process through a pipeline (11) and the devolatilized lactide polymer composition leaves the devolatilization process (10) in a pipeline (12). The devolatilized lactide composition is fed to a resin-finishing process (14). Within the resin-finishing process the polymer is solidified and processed to form a pelletized or granular resin or bead. Applicants recognize the polymer may be solidified and processed to form resin or bead first, followed by devolatilization. The resin is then fed to a drying process (16) by conveyance means (15). Within the drying process (16) moisture is removed as a vapor through pipeline (17). The dried lactide polymer resin leaves the drying process (16) by a conveyance means (18) and is fed to a melt-processing apparatus (19). Within the melt-processing apparatus (19) the resin is converted to a useful article as disclosed above. The useful article leaves the melt-processing apparatus (19) through a conveyance means (20).

The following examples further detail advantages of the system disclosed herein:

EXAMPLE 1

Melt Spinning of Poly(lactide)

Melt spinning of poly(lactide) having a weight average molecular weight of 140,000, a residual lactide content of about 1.1 percent and an original lactide mixture of about 7 percent by weight meso-lactide was performed on a 13 mm. single screw extruder with a gear pump and fitted with a 7 hole multifilament spinning head. The hole diameter was 0.4 mm. The spinline length, the distance from the spinning head to the take-up roll, was 1.7 meters. Polymer throughput was 1 g/min/hole. Filaments were drawn down by drawing through a circular aspirator which makes use of high velocity air to apply a force downward on the fibers. Post drawing of the fibers was also done on a draw stand or heated godet.

The process conditions were varied to find conditions under which fibers could be made from poly(lactide). Extrusion temperatures were varied from 150° to 170° C. and the take up velocity was varied from 500 to 6,000 meters/min. Fiber diameters were measured and are shown in Table 1 for the various fiber spinning conditions. With a microscope equipped with a light polarizer, birefringence was measured to assess the extent of polymer orientation within the fiber as a function of spinning conditions, Table 1 shows birefringence as a function of take-up velocity and fiber diameter as a function of take-up velocity respectively.

TABLE 1

| Take-up Velocity (meters/min) | Extrusion Temperature (°C.) | Fiber Diameter (microns) | Birefringence × 1000 |
|---|---|---|---|
| 2674 | 170 | 19.0 | 13.84 |
| 6179 | 160 | 12.5 | 15.84 |
| 4656 | 160 | 14.4 | 12.71 |
| 3177 | 160 | 17.6 | 9.09 |
| 4656 | 150 | 14.4 | 14.94 |
| 3421 | 150 | 16.8 | 8.04 |
| 3117 | 150 | 17.6 | 11.82 |
| 478 | 150 | 45.0 | 0.91 |

Fibers collected at a take-up velocity of 478 meters/min were post drawn on a heated godet. This apparatus is a series of rolls, including an unwind roll on the front and a take-up roll on the back. With the take up roll rotating faster than the unwind roll, the fiber is stretched. The rolls in between the unwind and take-up are heated to a temperature of 50° C. to soften the polymer and allow the fiber to be drawn. Measuring fiber diameter allows calculation of the draw ratio and birefringence relates to the degree of orientation of the polymer chains. Table 2 summarizes the drawing data. The data illustrates it is possible to postdraw the fibers to increase the orientation of the fibers.

TABLE 2

| Initial Diameter | Final Diameter | Draw Ratio | Birefringence × 1000 |
|---|---|---|---|
| 45.00 | 26.00 | 3.00 | 16.64 |
| 45.00 | 25.10 | 3.18 | 19.73 |
| 45.00 | 24.80 | 3.32 | 21.94 |
| 45.00 | 24.00 | 3.50 | 19.58 |

EXAMPLE 2

Properties of Poly(lactide) Melt Spun Fibers

In an apparatus similar to that used in Example 1, poly (lactide) having a weight average molecular weight of about 100,000, a residual lactide content of less than about 1 percent and an original lactide mixture of about 10 percent by weight of meso-lactide was melt spun into a fiber. The optical composition was such that upon annealing, (the sample was held at 100° C. for 90 minutes, the oven was turned off and was allowed to cool to room temperature), the polymer exhibited an endothermic melt peak with a peak temperature of 140° C. with an endotherm of 36.1 joules/gram.

The poly(lactide) fibers were post drawn as in Example 1. The thermal and mechanical properties are shown in Table 3. The results compare favorably to standard fiber resins such as polypropylene and nylon. The elongation and modulus compare favorably to commercial fibers. Further, poly (lactide) exhibited an affinity to crystallize under the conditions of fiber spinning.

TABLE 3

| Properties | Resin | As-Spun | Drawn | Polyprop. | Nylon 6,6 |
|---|---|---|---|---|---|
| Melt Temp (°C.) | 133 | 140 | 140 | 170 | 265 |
| Heat of Fusion (J/g) | 2.4 | 14.2 | 26.4 | 105 | xxxxx |
| Denier (g/9000 m) | xxxxx | 162 | 57 | xxxxx | xxxxx |
| Tenacity (g/den) | xxxxx | 0.97 | 2.75 | 6.5 | 5.4 |
| Break Elongation | xxxxx | 165% | 38% | 34% | 20% |
| Young's Modulus (g/den) | xxxxx | 22 | 44 | 68 | 34 |

EXAMPLE 3

Melt Blown Fabrics from Poly(lactide)

On a six inch melt blown nonwoven line equipped with a single screw extruder, poly(lactide) of a weight average molecular weight of about 80,000, a residual lactide content of about 0.6 percent, an original lactide mixture of about 9 percent by weight of meso-lactide and a water content of about 70 ppm was converted into melt blown nonwoven webs. This process involves feeding resin pellets into a feeding hopper of an extruder having a one inch single screw and extruding molten polymer through a die containing many small holes out of which emerges small diameter fiber. The fiber diameter is attenuated at the die as the fiber emerges using high velocity hot air. Three inches from the die exit is a rotating collection drum on which the fibrous web is deposited and conveyed to a wind up spool. The melt blown line is of standard design as in Malkan et al. (Nonwovens: An Advanced Tutorial, TAPPI press, Atlanta, 1989, pp 101–129). The die used had 121 holes with a diameter of 0.020 inch per hole.

Conditions were varied to find conditions under which poly(lactide) could be made into a useful nonwoven fabric. The die temperature was varied from 380° to 480° F., the air temperature was varied from 458° to 500° F., the die-to-collector distance varied from 6 to 14 inches and the air velocity varied from approximately 12 to 18 cu-ft/min/inch web.

The resultant poly(lactide) webs were tested for performance using standard tests for melt blown fabrics. The basic weight of all webs was 1 oz/sq-yd. Fiber diameter and fiber diameter variability were measured using a scanning electronic microscope. Tensile stress-strain properties were measured using ASTM method D-1682-64. Bursting strength was measured using the Mullen Bursting Tester and ASTM method D-3387. Filtration efficiency was assessed using an aerosol having 0.1 micron sodium chloride particles. The filtration test involved making a 20 gram/liter NaCl solution and making an aerosol of the solution with a concentration of 100 milligram per cubic meter. The aerosol was thereafter passed through the fabric at 31 liters/minute. Sensors were placed both upstream and downstream of the fabric, with the difference reflecting the amount remaining in the filter. Air permeability, another feature important to filtration, was measured according to ASTM D737-75 and reported as cubic feet of air per square feet of fabric per minute. All of these performance measures were compared to standard polypropylene fabrics. The data illustrates poly(lactide) processes as well as polypropylene. Poly(lactide) is capable of forming fine or small diameter fibers. Fibers having diameters of less than about 5 $\mu$m are shown. Further, poly (lactide) nonwoven webs have a high filtration efficacy as well as good air permeability. The results are shown in Table 4.

TABLE 4

| Sample | 1 | 2 | 3 | 4 | 5 | 6 | 7 | 8 | typical PP |
|---|---|---|---|---|---|---|---|---|---|
| Conditions: | | | | | | | | | |
| Die temp. °F. | 380 | 395 | 395 | 395 | 395 | 395 | 395 | 395 | 480 |
| Air temp. °F. | 446 | 446 | 446 | 446 | 446 | 460 | 460 | 458 | 500 |
| DCD inches | 10 | 10 | 10 | 6 | 14 | 10 | 14 | 10 | 12 |
| Air Valve rate | 40% | 40% | 50% | 50% | 50% | 60% | 60% | 55% | 40% |
| Property: | | | | | | | | | |
| Air Permeabil. ft3/ft2/min | 271 | 247 | 175 | 90 | 227 | 103 | 137 | 149 | 50–100 |
| Bursting strength, psi | 8.3 | 9.3 | 9.6 | 7.6 | 8.6 | 8.8 | 10.6 | 10.0 | 6–10 |
| Filtration Eff. % | 38.9 | 37.3 | 43.2 | 60.0 | 47.7 | 65.3 | 59.0 | 47.0 | 25–60 |
| Peak Load, lb/in. | 2.10 | 2.15 | 2.30 | 4.77 | 1.00 | 3.26 | 1.50 | 2.80 | 0.8–3.5 |
| Peak Elongation, % | 3.10 | 2.80 | 3.70 | 3.90 | 2.50 | 5.10 | 3.00 | 4.40 | 10–30 |
| Av. Fiber Dia. $\mu$m | 3.83 | xxxx | 2.88 | xxxx | xxxx | xxxx | 3.41 | xxxx | 2–4 |
| C.V. % Fiber Dia. | 32.61 | xxxx | 37.77 | xxxx | xxxx | xxxx | 37.03 | xxxx | 25–40 |

EXAMPLE 4

Melt Blow Nonwovens made from Poly(lactide)

Melt blown fabrics were made with poly(lactide) using the same equipment and procedure as in Example 3. The extrusion temperature was 320° F., screw speed was 8 rpm, die temperature was 315° F., air temperature and air velocity were at 400° F. and 12 cu ft/min/inch web respectively. Die-to-collector distance was 13 inches.

The poly(lactide) used in this test had a weight average molecular weight of about 66,000, a residual lactide concentration of about 1.3% and an original lactide mixture of about 9 percent by weight of meso-lactide. This lower molecular weight resulted in softer nonwoven fabrics than Example 3 and had good hand. Fiber diameters were measured and found to be 11.57 pm. Other tests done on this fabric was the air permeability test having a value of 4.26, bursting strength having a value of 5.4, and filtration efficiency having a value of 14.0 percent.

EXAMPLE 5

Anti-Blocking Agents

Two injection molded disks, 2.5 inch diameter, were placed together with a 94 gram weight on top and held at 50°

C. for 24 hours. The disks had the following agents compounded therein. The disks were then cooled to room temperature and pulled apart by hand and ranked for blocking characteristics (considerable, slight and none). The following are the results:

TABLE 5

| AGENTS | |
| --- | --- |
| Poly(lactide) control | considerable |
| 22% wheat gluten | none |
| 10% wheat gluten | slight |
| 22% pecan shell | none |
| 15% pecan shell | slight |
| 23% wollastonite | slight |
| 28% Ultratalc 609 | none |
| 23% Ultratalc 609 | none |
| 28% Microtuff F talc | slight |
| 22% Microtuff F talc | slight |
| 14% Microtuff F talc | slight |
| 2% Microtuff F talc | considerable |

EXAMPLE 6

Plasticizer Agents

Dried pellets of devolatilized poly(lactide) were processed in a twin screw extruder to allow compounding various plasticizing agents. The strands leaving the extruder were cooled in a water trough and chopped into Samples of the pellets were heated at 20 C./minutes to 200° C. in a DSC apparatus, held at 200° C. for 2 minutes and rapidly cooled to quench the samples. The quenched samples were then reheated in the DSC apparatus increasing at 20° C./minute to determine the glass transition temperature. These samples were compared to a polymer with no plasticizer. The effect of the plasticizer on the glass transition temperature is shown in the table below. Glass transition temperatures are taken at the mid-point of the transition.

TABLE 6

| SAMPLE | $T_g(C)$ | Change in $T_g$/wt. percent additive |
| --- | --- | --- |
| Control | 54.8 | — |
| 8% Dioctyl adipate | 35.0 | 2.5 |
| Control + 40% silica | 54.5 | — |
| Control + 40% silica + 5% dioctyl adipate | 36.0 | 3.7 |
| Control | 54.6 | — |
| 6% Citroflex A-4* | 42.6 | 2.0 |
| 12% Citroflex A-4 | 31.4 | 1.9 |
| Control | 59.3 | — |
| 1.6% Citroflex A-4 | 56.3 | 1.9 |
| 2.9% Citroflex A-4 | 53.1 | 2.1 |
| Control | 58.4 | — |
| 2.1% Citroflex A-4 | 56.1 | 1.1 |
| 3.4% Citroflex A-4 | 50.5 | 2.3 |
| Control | 61.6 | — |
| 18.6% Citroflex A-2 | 54.7 | 0.4 |
| 13.1% Citroflex B-6 | 52.4 | 0.7 |
| 12.6% Citroflex A-6 | 53.8 | 0.6 |

These results show the effectiveness of these plasticizers in reducing the glass transition temperature of poly(lactide).

The procedure above was tried using corn oil as a plasticizer. Visual observation showed the corn oil to be not compatible, forming a film on the surface. Corn oil and mineral oil were both not effective as a primary plasticizer with poly(lactide). They may still be useful as a secondary plasticizer, in combination with a compatible primary plasticizer.

EXAMPLE 7

Lactide and Poly(lactide) Equilibrium Concentrations

Experiments were conducted to determine the equilibrium concentration of lactide and poly(lactitemperatureerent temperatures. In these experiments a sample of lactide was polymerized in the presence of a catalyst (tin (II) bis(2-ethyl hexanoate)) and held at a fixed temperature for 18 hours or greater. Beyond this time the residual monomer concentration is believed essentially constant. The content of residual monomer was determined by GPC analysis. GPC analysis was conducted with an Ultrastyragel® column from Waters Chromatography. The mobile phase was chloroform. A refractive index detector with molecular weight calibration using polystyrene standards was used. The GPC temperature was 35° C. Data analysis was completed using the software package Baseline, model 810, version 3.31.

Figure 2:
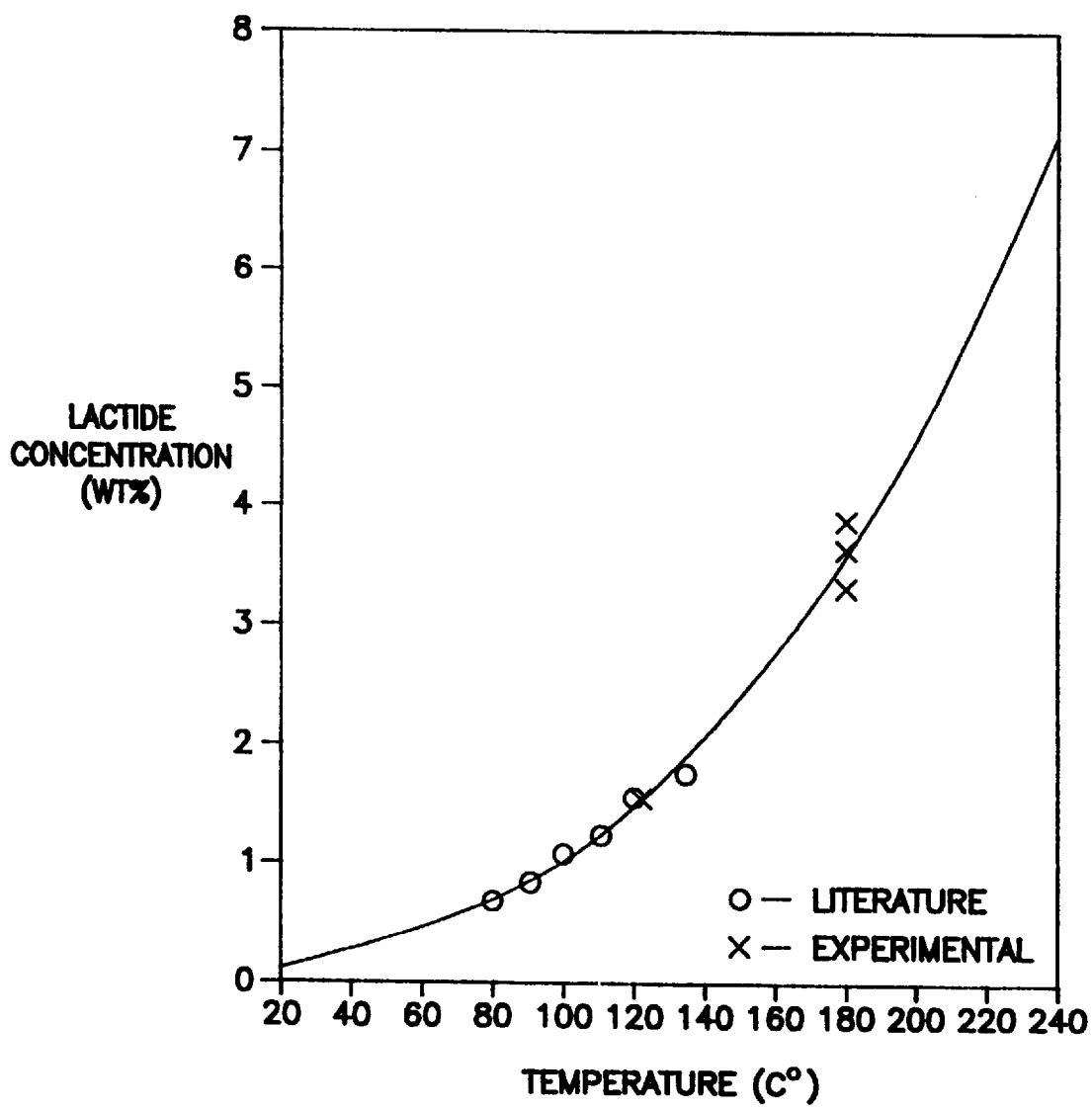
FIG. 2 is a graph showing the equilibrium relationship between lactide and poly(lactide) at various temperatures

The results of tests conducted on several samples at various temperatures are summarized in the graph of FIG. 2 as indicated by X's on such graph. Also plotted on the graph of FIG. 2 are data points cited in A. Duda and S. Penczek, *Macromolecules,* vol. 23, pp. 1636–1639 (1990) as indicated by circles on the graph. As can be seen from the graph of FIG. 2, the equilibrium concentration, and thus the driving force behind the depolymerization of poly(lactide) to form lactide, increases dramatically with increased temperature. Thus, melt-processing at elevated temperatures results in degradation of the lactide polymer to form lactide on the basis of equilibrium alone. For example, lactide concentrations below about 2 percent cannot be directly obtained at temperatures of 140° C. or above due to the identified equilibrium relationship between lactide and poly(lactide).

EXAMPLE 8

Lactide Polymerization in the Presence of a Solid Supported Catalyst

Tin (II) Oxide 24 grams of L-lactide (melting point about 97° C.) and 6 grams of D,L-lactide (for the purposes of this invention, D,L-lactide has a melting point of about 126° C.) were combined in a round bottom flask with 0.033 grams of Tin (II) oxide, as a fine powder. This corresponds to the catalyst level of 852:1, molar ratio lactide to tin. The flask was then purged with dry nitrogen 5 times. This was lowered into an oil bath at 160° C. with magnetic stirring. Polymerization time was 8 hours.

Amberlyst 36

24 grams of L-lactide and 6 grams of D,L-lactide were combined in a round bottom flask with 1.06 grams of Amberlyst 36 resin beads. The flask was purged 5 times with dry nitrogen. The flask was lowered into an oil bath at 140° C. with magnetic stirring. Polymerization time was 8 hours. The resin had a stated proton content of 1 meq/gram dry weight resin. The resin was prepared by rinsing 2 times with 10 volumes dry methanol, then dried for several hours under high vacuum for several hours at 40° C.

The polymerization results are shown below:

TABLE 7

| Sample | Mn | Mw | PDI | % Conversion |
|---|---|---|---|---|
| Tin (II) Oxide | 77,228 | 103,161 | 1.34 | 54.0 |
| Amberlyst | 1,112 | 1,498 | 1.34 | 73.5 |

EXAMPLE 9

Molecular Weight Relationship to Physical Properties of Lactide Polymers

Poly(lactide) samples with various molecular weights and optical compositions were prepared by polymerizing blends of L-lactide and meso-lactide at 180° C. under nitrogen in a 1-gallon sealed reactor. Tin(II) bis(2-ethyl hexanoate) catalyst was added at a monomer-to-catalyst ratio of 10,000:1. After about 1 hour the molten polymer was drained from the reactor using nitrogen pressure. The sample was poured into a pan and placed in a vacuum oven at about 160° C. for about 4 hours to bring the reaction to near equilibrium levels.

Portions of the samples were then dried under vacuum and processed in an injection molding apparatus (New Britain 75 from New Britain Machine Co.) to produce standard test bars for physical property testing. The results of physical property testing are shown in the following Table 8. The physical property tests were made according to ASTM methods D 638, D 256, and D 790. The reported results are the averages of several tests.

Samples of the test bars after injection molding were analyzed by GPC for molecular weight. Other portions of the test bars were reground and tested in a capillary viscometer to determine the melt-viscosity. These results are also included in Table 8.

Statistical analysis of the data revealed no correlations which were statistically significant between either optical composition or molecular weight and the mechanical properties of modulus, tensile strength, percentage elongation at break, notched Izod impact strength, flexural modulus, or flexural strength. The independence of these properties on molecular weight indicates that all of these samples were above a "threshold" molecular weight required to achieve the intrinsic properties of the polymer in a preferred composition.

The viscosity data show significant correlations with molecular weight. This dependence documents the practical limitation and necessity of controlling polymer molecular weight below an upper limit at which it is impractical to melt-process the polymer. At high molecular weight, high viscosity prevents processing by standard melt-processing equipment. Increases in temperature to reduce viscosity dramatically increase polymer degradation and lactide formation which is also unacceptable.

TABLE 8

| Sample I.D. | Meso Lactide In Blend, Wt % | Molecular Weight After Injection Weight | Final IV (dl/g) | Viscosity at 173° C. (Pa · S) Shear Rate 100 S$^{-1}$ | Shear Rate 1000 S$^{-1}$ |
|---|---|---|---|---|---|
| 6 | 40 | 41000 | 0.86 | 5.5 | 2.9 |
| 5 | 10 | 54000 | 0.88 | 10.4 | 7.2 |
| 4 | 20 | 59000 | 0.91 | 10.4 | 7.2 |
| 8 | 10 | 64000 | 1.02 | 15.7 | 10.0 |
| 9 | 40 | 68000 | 0.97 | 12.6 | 8.1 |
| 7 | 20 | 71000 | 1.16 | 36.0 | 12.9 |
| 10 | 20 | 83000 | 1.19 | 35.8 | 15.8 |

Mechanical Properties of Injection Molded Samples

| Sample I.D. | Modulus MPSI | Tensile Strength (Yld) PSI | % Elongation at Break | IZOD Impact ft · lb./in | Flexural Modulus MPSI | Flexural Strength PSI |
|---|---|---|---|---|---|---|
| 6 | 0.55 | 6600 | 3.3 | 0.39 | 0.53 | 11300 |
| 5 | 0.56 | 7800 | 3.5 | 0.46 | 0.54 | 12500 |
| 4 | 0.56 | 7600 | 3.9 | 0.32 | 0.53 | 12500 |
| 8 | 0.55 | 7700 | 3.4 | 0.47 | 0.53 | 12400 |
| 9 | 0.59 | 6700 | 3.1 | 0.42 | 0.52 | 10600 |
| 7 | 0.56 | 7400 | 3.3 | 0.45 | 0.51 | 12400 |
| 10 | 0.55 | 6700 | 3.0 | 0.47 | 0.52 | 9900 |

EXAMPLE 10

Effect of Residual Catalyst on Polymer Degradation

Polymer samples were prepared at four levels of catalyst, corresponding to monomer to catalyst molar ratios of 5,000:1, 10,000:1, 20,000:1, and 40,000:1. The catalyst utilized was tin (II) bis(2-ethyl hexanoate). These samples were then subjected to heating in a TGA apparatus (TA Instruments, Inc., model 951 thermogravometric analyzer with a DuPont 9900 computer support system) with a nitrogen purge. Isothermal conditions of 200° C. for 20 minutes were used. The samples were then analyzed by GPC with a viscosity-based detector and a universal calibration curve to determine the extent of breakdown in molecular weight. The GPC apparatus for this test was a Viscotek Model 200 GPC and a Phenomenex column. The TGA analysis typically resulted in about a 5 percent loss in weight and molecular weight drops of 0 to 70 percent.

The number average molecular weights were converted to a milliequivalent per kilogram basis (1,000,000/Mn) in order to calculate a rate of chain scission events. The results below represent averages of 2–4 replicates on each of the four samples.

TABLE 9

| Catalyst level (monomer/catalyst) | Scission Rate (meq/kg*min) |
|---|---|
| 5,000 | 1.33 |
| 10,000 | 0.62 |
| 20,000 | 0.44 |
| 40,000 | 0.12 |

The rate of chain scission was directly proportional to the residual catalyst level, demonstrating the detrimental effect of catalyst activity on melt-stability under conditions similar to melt-processing. This instability, however, is distinguished from the instability due to the equilibrium relationship between lactide and poly(lactide) detailed in Example 7, in that loss of molecular weight due to catalytic depolymerization by chain scission is evident.

EXAMPLE 11

Catalyst Deactivation Experiment

Two runs were made in a laboratory Parr reactor. Lactide feed was 80 percent L-lactide and 20 percent D,L-lactide.

Molecular weight was controlled by adding a small quantity of lactic acid, the target molecular weight was 80,000 Mn.

Lactide was charged to the reactor as a dry mix, the reactor was purged 5 times with nitrogen, and heated up to 180° C. At this point catalyst (5000:1 initial monomer to catalyst molar ratio, Fascat® 2003) was charged through a port in the top of the reactor. The reaction was allowed to proceed for 70 minutes at 180° C., with mechanical agitation. Conversion at this point was 93–94 percent, close to the equilibrium value at 180° C. of 96 percent poly(lactide) from FIG. 2. This point is considered tzero, designating the completion of the polymerization reaction and the beginning of the mixing time.

In the control experiment, a sample was taken and the mixture was held at temperature with continued agitation. Samples were taken periodically through a port in the reactor bottom. After 4 hours the reactor was drained.

In the example experiment, a sample was taken and 0.25 weight percent of a metal deactivator (Irganox® MD 1024®) was added through the catalyst addition port. The mixture was held at temperature with continued agitation and samples were withdrawn periodically. The reactor was drained after 4 hours.

GPC analysis (utilizing the method of Example 7) for these samples was divided into three parts: polymer with molecular weight over 4,000 (for which the Mn and Mw numbers are reported), the percent oligomers (comprising the region with molecular weight greater than lactide but less than 4,000, as distinguished from oligomers as defined by Loomis to include only oligomers up to a molecular weight of 450), and percent lactide (residual monomer). The structure of the oligomers was not certain, but it is believed they were primarily cyclic structures. It is also believed that the metal deactivator, if unreacted, will elute with the oligomer fraction. Quantification of the oligomer fraction is difficult, because the GPC trace is near the baseline in this region.

The analysis of the polymer samples as withdrawn from the reactor at various time intervals for the control and experimental compositions are shown below in Table 10.

TABLE 10

| Control | Mn | Mw | % Polymer | % Oligomer | % Monomer |
|---|---|---|---|---|---|
| t-zero | 67,100 | 119,500 | 94 | 0 | 6.0 |
| 0.5 hr | 62,500 | 119,000 | 95 | 0.7 | 3.9 |
| 1.0 hr | 61,500 | 116,100 | 96 | 0 | 3.6 |
| 1.5 hr | 56,000 | 111,600 | 95 | 1.5 | 3.3 |
| 2.0 hr | 57,600 | 110,900 | 96 | 0.9 | 3.1 |
| 4.0 hr | 51,400 | 105,400 | 94 | 3.3 | 3.1 |
| Test | Mn | Mw | % Polymer | % Oligomer | % Monomer |
| t-zero | 63,200 | 110,700 | 93 | 3.5 | 3.8 |
| 0.5 hr | 52,100 | 108,600 | 92 | 4.6 | 2.9 |
| 1.0 hr | 52,700 | 109,200 | 92 | 4.9 | 2.8 |
| 1.5 hr | 53,400 | 107,200 | 93 | 4.0 | 3.1 |
| 2.0 hr | 59,700 | 111,100 | 94 | 0.6 | 5.8 |
| 4.0 hr | 51,200 | 107,300 | 91 | 6.1 | 3.3 |

The samples were then ground and placed in a 120° C. oven under vacuum (pressure 0.1 inch Hg) for 14 hours. Sample analyses after this treatment are shown below in Table 11.

TABLE 11

| Control | Mn | Mw | % Polymer | % Oligomer | % Monomer |
|---|---|---|---|---|---|
| t-zero | 45,500 | 88,500 | 98 | 2.2 | 0.0 |
| 0.5 hr | 45,000 | 88,700 | 98 | 2.0 | 0.0 |
| 1.0 hr | 43,900 | 87,200 | 98 | 2.0 | 0.0 |
| 1.5 hr | 42,600 | 84,000 | 98 | 2.2 | 0.0 |
| 2.0 hr | 42,000 | 85,200 | 97 | 3.2 | 0.0 |
| 4.0 hr | 41,900 | 82,800 | 98 | 2.0 | 0.0 |
| Test | Mn | Mw | % Polymer | % Oligomer | % Monomer |
| t-zero | 39,300 | 76,700 | 96 | 4.0 | 0.0 |
| 0.5 hr | 43,900 | 85,100 | 98 | 2.4 | 0.0 |
| 1.0 hr | 55,300 | 98,600 | 96 | 3.8 | 0.0 |
| 1.5 hr | 48,400 | 96,200 | 95 | 4.5 | 0.0 |
| 2.0 hr | 48,900 | 101,900 | 95 | 5.0 | 0.0 |
| 4.0 | 50,600 | 101,900 | 94 | 5.6 | 0.0 |

In all cases the polymer was completely devolatilized (0.0 percent residual lactide monomer). The data also clearly show that the metal deactivator reduced the degradation of polymer during the devolatilization step (as indicated by the greater loss in Mn for the control samples from Table 9 to Table 10 versus the Test samples). One hour of mixing appears to be long enough to develop most of the benefit.

The samples were stored at room temperature under nitrogen for about 1 week and reanalyzed, as shown below in Table 12.

TABLE 12

| Control | Mn | Mw | % Polymer | % Oligomer | % Monomer |
|---|---|---|---|---|---|
| t-zero | 33,500 | 71,000 | 100 | 0.1 | 0.0 |
| 0.5 hr | 43,400 | 95,800 | 99 | 1.0 | 0.0 |
| 1.0 hr | 44,900 | 96,300 | 100 | 0.1 | 0.0 |
| 1.5 hr | 45,900 | 95,000 | 100 | 0.0 | 0.0 |
| 2.0 hr | 45,900 | 94,100 | 100 | 0.2 | 0.0 |
| 4.0 hr | 43,100 | 90,100 | 99 | 1.3 | 0.0 |
| Test | Mn | Mw | % Polymer | % Oligomer | % Monomer |
| t-zero | 44,600 | 84,900 | 100 | 0.0 | 0.0 |
| 0.5 hr | 45,300 | 90,600 | 99 | 1.2 | 0.0 |
| 1.0 hr | 47,800 | 100,000 | 98 | 2.4 | 0.0 |
| 1.5 hr | 46,600 | 98,900 | 96 | 3.5 | 0.0 |
| 4.0 | 57,700 | 110,200 | 96 | 4.0 | 0.3 |

Equilibrium lactide levels are estimated to be less than 0.2 weight percent at room temperature. Consistent with that, essentially no lactide was observed in any of the samples (detection limit about 0.1 weight percent). The oligomer content in the non-stabilized samples declined and some increase in molecular weight was noted, perhaps due to reincorporation of the (cyclic) oligomers into the polymer. The oligomer depletion reaction was inhibited in the stabilized polymers, with the extent of inhibition dependent on the length of time that the additive was mixed.

The samples were then reheated to 180° C. in sealed vials and held for one hour as a simulation of melt-processing. Analysis of the samples after the heat treatment is given below in Table 13.

TABLE 13

| Control | Mn | Mw | % Polymer | % Oligomer | % Monomer |
|---|---|---|---|---|---|
| t-zero | 23,900 | 60,000 | 88 | 8.4 | 4.0 |
| 0.5 hr | 23,900 | 59,600 | 90 | 7.7 | 2.7 |

TABLE 13-continued

| | | | | |
|---|---|---|---|---|
| 1.0 hr | 23,700 | 58,800 | 88 | 9.3 | 2.7 |
| 1.5 hr | 24,700 | 58,000 | 86 | 10.0 | 3.8 |
| 2.0 hr | 26,100 | 56,400 | 90 | 6.8 | 2.7 |
| 4.0 hr | 24,800 | 58,700 | 92 | 6.6 | 1.9 |

| Test | Mn | Mw | % Polymer | % Oligomer | % Monomer |
|---|---|---|---|---|---|
| t-zero | 33,900 | 64,300 | 95 | 2.2 | 3.1 |
| 0.5 hr | 17,900 | 34,600 | 94 | 4.8 | 1.7 |
| 1.0 hr | 21,200 | 42,900 | 94 | 4.6 | 1.8 |
| 1.5 hr | 29,200 | 56,900 | 98 | 0.5 | 1.8 |
| 2.0 hr | missing | | | | |
| 4.0 hr | 35,700 | 71,400 | 95 | 3.7 | 1.7 |

The data for molecular weight show that if the metal deactivator is not mixed into the system long enough then it can have a detrimental impact on stability in the melt. The samples for which the mixing was at least 1.5 hours show no detrimental effect, and the 4 hour sample appears to be somewhat more stable than any of the others based on molecular weight alone. More importantly, the metal deactivator samples show significantly less lactide reformation than the control samples. This effect is gained even in the samples which were mixed for only 0.5 hour. The metals deactivated samples averaged only 1.8 percent lactide after one hour at 180° C., compared to an average of 3.0 percent lactide for the controls. The equilibrium level at 180° C. is about 3.6 percent from FIG. 2. Thus, the use of metal deactivators can reduce the troublesome reformation of lactide during melt-processing of the finished polymer.

EXAMPLE 12

Effect of Increased Polymerization Temperature on Polymer Characteristics

L-lactide (Boeringer Ingleheim, S-grade) was used as received, meso-lactide (PURAC) was purified by distillation to remove traces of D- and L-lactide. The melting point of the purified meso-lactide was 54° C. Lactide mixtures were made up to the following ratios: 100 percent L-lactide, 90/10 L-lactide/meso-lactide, 70/30 L-lactide/meso-lactide, 50/50 L-lactide/meso-lactide, and 100 percent meso-lactide. Catalyst level was 2,500:1 molar ratio of initial monomer to tin with the tin being tin(II) bis (2-ethyl hexanoate) (Fascat® 9002). Lactic acid was added as a molecular weight control agent to target a number average molecular weight of 50,000 (the same amount was added to all samples). Polymerization times were estimated to obtain conversions of 50 percent and 90 percent. For 120° C. this was 4 hours and 16 hours, respectively. For 180° C. these times were 10 minutes and 50 minutes, respectively. Below in Table 14 are the GPC results (method of Example 7) of tests on the polymer samples produced by this procedure.

TABLE 14

| L/meso | Temp | Mn | Mw | PDI | % Conv |
|---|---|---|---|---|---|
| 100% L | 120° C. | 31,014 | 33,774 | 1.09 | 53.2 |
| | | 45,864 | 52,574 | 1.15 | 87.1 |
| 100% L | 180° C. | 27,785 | 32,432 | 1.17 | 46.7 |
| | | 56,839 | 98,125 | 1.73 | 93.3 |
| 90/10 | 120° C. | 34,541 | 38,586 | 1.12 | 62.3 |
| | | 29,222 | 34,466 | 1.18 | 89.3 |
| 90/10 | 180° C. | 31,632 | 35,713 | 1.13 | 48.5 |
| | | 57,925 | 110,841 | 1.91 | 94.8 |
| 70/30 | 120° C. | 41,211 | 45,222 | 1.10 | 60.1 |

TABLE 14-continued

| L/meso | Temp | Mn | Mw | PDI | % Conv |
|---|---|---|---|---|---|
| | | 58,284 | 71,257 | 1.22 | 89.1 |
| 70/30 | 180° C. | 32,292 | 37,401 | 1.16 | 53.8 |
| | | 51,245 | 107,698 | 2.10 | 96.5 |
| 50/50 | 120° C. | 15,888 | 17,969 | 1.13 | 57.8 |
| | | 25,539 | 31,834 | 1.25 | 90.6 |
| 50/50 | 180° C. | 34,375 | 42,018 | 1.22 | 62.5 |
| | | 44,590 | 98,028 | 2.20 | 95.5 |
| 100% meso | 120° C. | 33,571 | 40,635 | 1.21 | 73.4 |
| | | 45,237 | 68,142 | 1.51 | 94.3 |
| 100% meso | 180° C. | 30,976 | 42,987 | 1.39 | 67.6 |
| | | 40,038 | 83,815 | 2.09 | 96.6 |

The results show that the ultimate number average molecular weight was not significantly affected by the temperature of polymerization, with an average of 41,000 at 120° C. and 50,000 at 180° C. This implies that each lactic acid molecule initiates about one polymer chain, regardless of temperature. The ultimate weight average molecular weight is, however, significantly affected by temperature. At 120° C. the weight average molecular weight averaged 52,000 and at 180° C. the was 100,000. This is believed to be due to a relative increase in the rate of transesterification at 1.80° C. The polydispersity index (PDI) at high conversion also reflects this, averaging 1.3 at 120° C. and 2.0 at 180° C. It is believed these differences would have a significant effect on the melt-processing characteristics of the polymer, with the higher weight average molecular weight of the polymer produced at 180° C. expected to translate into better melt strength and processability.

These experiments show that polymerization at a higher temperature results in a polymer that is characteristically different. Further, the glass transition temperature for the samples polymerized at higher temperature is higher.

EXAMPLE 13

Experiments with Stabilizing Agents and Metal Deactivators

Test 1

Conditions: vial polymerization, (Lactide is melted under a nitrogen-purged atmosphere in a round bottom flask with stirring. Catalyst and additives are added and aliquots of the mixtures are pipetted into silanized glass vials. Typically 5–10 grams of reaction mixture are used in a 16 ml. vial. The vials are tightly capped and placed into a preheated oil bath.) 10,000:1 molar ratio of lactide-to-tin, tin(II) bis(2-ethyl hexanoate) catalyst, 0.2 weight percent Ultranox® 626 in tetrahydrofuran (THF). 180° C. Time was 90 minutes.

The control with tin only polymerized to 84 percent conversion and reached a MWn of 31,700. The example with tin and Ultranox® polymerized to 83 percent conversion and reached a number average molecular weight (MWn) of 39,800; an increase of 26 percent over the control.

The control sample turned light yellow, the sample with stabilizer remained colorless.

Test 2

Conditions: vial polymerization, 5000:1 molar ratio of lactide to tin, tin(II) bis(2-ethyl hexanoate) catalyst, 0.25 wt percent Ultranox® 626 (in THF). 180° C. Time was 60 minutes. Lactide was used from the above described Gruber et al. process.

The control with tin alone polymerized to 67 percent conversion and reached a MWn of 62,900. The example with tin and Ultranox® polymerized to 66 percent conversion and reached a MWn of 75800; an increase of 21 percent over the control.

A second example with tin(II) bis(2-ethyl hexanoate), Ultranox®, and 0.50 percent of Irganox® 1076, which is a phenolic antioxidant, polymerized to 66 percent conversion and reached a number average molecular weight (MWn) of 74500; an increase of 18 percent over the control.

All samples were a dark yellow color, although the samples with stabilizer had a slightly lower absorbance at 300 nm.

Test 3

Conditions: vial polymerization, 10,000:1 molar ratio of lactide to tin, tin(II) bis(2-ethyl hexanoate) catalyst, 180° C., 80 percent L-lactide and 20 percent D,L-lactide purchased from Henley and Aldrich, respectively. Lactic acid was added to control molecular weight to about 75,000 at full conversion One sample included 0.25 percent Ultranox® 626 phosphite stabilizer, one included 0.25 percent Irganox® 1076 antioxidant, and one control sample.

Samples were taken at various times and analyzed by GPC for conversion and molecular weight (the method of Example 7). The results are summarized in Table 15 below.

TABLE 15

| Time  | Control |        | Irganox ® |        | Ultranox ® |        |
|-------|---------|--------|-----------|--------|------------|--------|
| (hrs) | Mn      | % conv | Mn        | % conv | Mn         | % conv |
| 1     | 31,000  | 46     | 35,900    | 41     | 66,500     | 61     |
| 2     | 45,400  | 74     | 56,800    | 74     | 102,700    | 83     |
| 4     | 69,600  | 93     | 74,100    | 93     | 97,200     | 91     |
| 11    | 52,900  | 95     | 60,700    | 95     | 71,500     | 94     |

The sample with phosphite stabilizer polymerized faster, shown by the higher conversion at 1 and 2 hours, and went to a higher molecular weight than the control or the sample with Irganox®. The phosphite stabilized sample had a molecular weight more than 30 percent higher than the control for all time periods.

Test 4

The experiment above was repeated to compare the control to the phosphite-stabilized polymer, as summarized in Table 16 below.

TABLE 16

| Time  | Control |        | Ultranox ® |        |
|-------|---------|--------|------------|--------|
| (hrs) | Mn      | % conv | Mn         | % conv |
| 1     | 36,600  | 37     | 71,500     | 59     |
| 2     | 51,700  | 70     | 95,200     | 85     |
| 4     | 64,400  | 91     | 103,700    | 94     |
| 8     | 58,100  | 96     | 95,700     | 94     |

The sample with phosphite stabilizer again polymerized faster and went to a higher molecular weight than the non-stabilized sample. The phosphite stabilized sample had a molecular weight more than 60% higher than the control for all time periods.

Test 5

Conditions: vial polymerization, 5,000:1 molar ratio of lactide to tin, tin(II) bis(2-ethyl hexanoate) catalyst, 180° C., 80 percent L-lactide and 20 percent D,L-lactide purchased from Henley and Aldrich. Lactic acid was added to control number average molecular weight to an estimated 80,000 at full conversion. One sample was run with 0.25 percent Ultranox® 626 phosphite stabilizer, one with 0.25 percent Irganox® 1076 antioxidant, and one control sample.

Samples taken at various times and analyzed by GPC (the method of Example 1) for conversion and molecular weight. The results are tabulated in Table 17 below.

TABLE 17

| Time  | Control |        | Irganox ® |        | Ultranox ® |        |
|-------|---------|--------|-----------|--------|------------|--------|
| (hrs) | Mn      | % conv | Mn        | % conv | Mn         | % conv |
| 1     | 83,600  | 76     | 121,900   | 83     | 162,300    | 87     |
| 4     | 74,400  | 93     | 104,300   | 95     | 123,900    | 96     |
| 24    | 40,200  | 96     | 52,000    | 96     | 96,900     | 97     |
| 48    | 34,200  | 97     | 30,400    | 96     | 56,500     | 96     |
| 72    | 25,000  | 96     | 22,400    | 96     | 69,500     | 96     |

The phosphite-stabilized sample had a molecular weight more than 60 percent higher than the control for all time periods. After 72 hours it had a molecular weight 2.8 times higher than the control. The sample with antioxidant showed an initial increase in molecular weight, relative to the control, but the effect disappeared after 48 hours.

The phosphite stabilized sample was significantly lighter in color than the control or the antioxidant treated sample.

Test 6

Conditions: vial polymerization, 5000:1 molar ratio of lactide to tin, tin(II) bis(2-ethyl hexanoate) catalyst, 0.25 wt percent Ultranox® 626 (in THF). 180° C. Time was two hours. Gruber et al. process lactide washed with isopropyl alcohol was used.

The control with tin alone polymerized to 95 percent conversion and reached a number average molecular weight of 118,000. The example with tin and Ultranox® polymerized to 93 percent conversion and reached a number average molecular weight of 151,000, an increase of 28 percent over the control.

Test 7

Conditions: vial polymerization at 180° C. 5000:1 molar ratio of lactide to tin, tin(II) bis(2-ethyl hexanoate) catalyst. Lactide was 80 percent L-lactide and 20 percent D,L-lactide, purchased from Henley and from Aldrich. Lactic acid was added to target the molecular weight to an Mn of 80,000. All stabilizers were added at 0.25 weight percent. Molecular weight (number average) was determined for samples pulled at 3 hours, while rate constants were based on samples pulled at 1 hour. The results of these screening tests on many stabilizing agents following the above procedure are detailed below in Table 18. Product designations in Table 18 are tradenames or registered trademarks.

TABLE 18

| Sample       |      | MWn     | % Conversion | Relative Rate |
|--------------|------|---------|--------------|---------------|
| Control 1    |      | 65,000  | 95.9         | 90            |
| Control 2    |      | 85,000  | 95.9         | 100           |
| Control 3    |      | 76,000  | 96.6         | 100           |
| Control 4    |      | 69,000  | 96.2         | 100           |
| Control 5    |      | 74,000  | 96.8         | 110           |
| Control 6    |      | 70,000  | 97.2         | 110           |
| PHOSPHITES   |      |         |              |               |
| Ultranox 626 | (GE) | 103,000 | 96.8         | 100           |
| Weston TDP   | (GE) | 64,000  | 70.0         | 60            |
| Weston PDDP  | (GE) | 67,000  | 76.7         | 60            |

TABLE 18-continued

| Sample | | MWn | % Conversion | Relative Rate |
|---|---|---|---|---|
| Weston PNPG | (GE) | 92,000 | 94.1 | 100 |
| Irgafos 168 | (Ciba-Geigy) | 95,000 | 95.3 | 120 |
| Weston 618 | (GE) | 99,000 | 95.1 | 100 |
| Sandostab P-EPQ | (Sandoz) | 108,000 | 94.7 | 110 |
| Weston TNPP | (GE) | 88,000 | 97.9 | 130 |
| PHENOLIC ANTIOXIDANTS | | | | |
| Irganox 1010 | (Ciba-Geigy) | 95,000 | 97.5 | 110 |
| Cyanox 1790 | (Cyanamid) | 98,000 | 96.9 | 120 |
| BHT | | 87,000 | 96.5 | 130 |
| Irganox 1076 | (Ciba-Geigy) | 121,000 | 97.8 | 130 |
| Topanol CA | (ICI) | 84,000 | 96.6 | 160 |
| AMINES | | | | |
| Tinuvin 123 | (Ciba-Geigy) | 65,000 | 94.8 | 70 |
| Tinuvin 622 | (Ciba-Geigy) | 82,000 | 95.7 | 80 |
| Naugard 445 | (Uniroyal) | 93,000 | 98.2 | 120 |
| THIOETHER | | | | |
| Mark 2140 | (Witco) | 77,000 | 97.0 | 120 |
| METAL DEACTIVATORS | | | | |
| Irganox MD1024 | (Ciba-Geigy) | 34,000 | 65.7 | 10 |
| Naugard XL-1 | (Uniroyal) | 91,000 | 95.8 | 110 |

Note, that with a few exceptions, the phosphites and the phenolic antioxidants provide increased molecular weight with no reduction in polymerization rate. Of the amines, only Naugard® 445 provided stabilization without a rate decrease. The metal deactivators are expected to deactivate the catalyst, as was observed for Irganox® MD1024. The Naugard® XL-1 did not accomplish deactivation.

EXAMPLE 14

Polymer Melt Stability as a Function of Moisture Content

Lactide, produced and purified in a continuous (Gruber et al.) process, was fed at a rate of 3 kg/hr to a continuous polymerization pilot plant. Catalyst was added with a metering pump at the rate of 1 part catalyst to 5000 parts lactide on a molar basis. The reaction system was blanketed with nitrogen. The reactor vessels consist of two continuous stirred tank reactors (CSTR) in series. The first had a 1-gallon capacity and the second had a 5-gallon capacity. The reactors were run 60–80 percent liquid filled and at 170°–180° C. Polymer melt pumps moved the liquid from CSTR 1 to CSTR 2, and from CSTR 2 through a die into a cooling water trough. The polymer strand thus produced was pulled from the trough by a pelletizer and stored as pellets.

The pelletized poly(lactide) was put into a drying hopper and dried at 40° C. under flowing dry air. Samples were pulled after one hour and four hours. These samples were then run through a single screw Brabender® extruder, with a retention time of approximately 3 minutes. Samples were analyzed for moisture by an automatic Karl Fischer apparatus and for molecular weight by GPC (the method of Example 7). The results of these tests are documented in Table 19 below.

TABLE 19

| Sample | Extruder Temperature (C.) | Weight Average Molecular Weight |
|---|---|---|
| Initial | | 63,000 |
| Dried 1 hour | 137 | 44,000 |
| (1200 ppm H$_2$O) | 145 | 48,000 |
| | 162 | 35,000 |
| | 179 | 30,000 |
| Dried 4 hours | 140 | 63,000 |
| (150 ppm H$_2$O) | 140 | 69,000 |
| | 160 | 65,000 |
| | 178 | 68,000 |

These results show the detrimental effect of water in the lactide polymer resin during melt polymerization and the need to properly dry the poly(lactide) before melt-processing.

EXAMPLE 15

Degradation of Crystalline and Amorphous Poly (lactide)

Two literature references disclose poly(D,L-lactide) to degrade faster than poly(L-lactide), attributing the result to crystallinity of poly(L-lactide). These are: Kulkarni et al., *J. Biomed. Mater. Res.*, vol. 5, pp. 169–181, (1971); Makino et al., *Chem. Pharm. Bull.*, vol. 33, pp. 1195–1201, (1985). An experiment was conducted to measure the effect of crystallinity on polymer degradation and is detailed below.

An amorphous poly(lactide) sample (clear, and less than 1 percentcrystallinity based on DSC) and a crystalline poly(lactide) sample (opaque, and approximately 50 percent crystallinity based on DSC) were subjected to biodegradation in a compost test (50° C., with aeration). The DSC apparatus was a TA Instruments, Inc., model 910 differential scanning calorimeter with DuPont 9900 computer support system typically programmed to heating at a rate of 10° C. per minute to 200° C. The samples had different optical composition, with the crystalline sample being, Lore than 90 percent poly(L-lactide) and the amorphous sample being less than 80 percent poly(L-lactide) with the balance being either poly(D,L-lactide) or poly(meso-lactide). Samples of each polymer were subjected to a compost test (ASTM D 5338) which included mixing a stabilized compost and providing a source of humidified air while maintaining a temperature of about 50° C. The amorphous sample was completely degraded after 30 days of composting. The crystalline sample was only 23 percent degraded based on carbon dioxide after the same period of time.

Additional samples of these two polymers were subjected to chemical hydrolysis at 50° C. (hydrolysis is believed to be the rate-limiting step in the biodegradation process). The chemical hydrolysis procedure included placing 0.1 gram poly(lactide) in 100 ml of 0.2M phosphate buffer (pH 7.4). The samples were held for 1 week, then filtered, washed with deionized water, and dried at 25° C. under vacuum. The initial weight average molecular weight for each sample was about 70,000. After 1 week the amorphous had a weight average molecular weight of 10,000 and crystalline sample had a weight average molecular weight of 45,000, determined by GPC (the method of Example 7). Neither sample had significant weight loss at this time.

Both of these tests demonstrate that degradation of crystalline poly(lactide) is slower than degradation of amorphous poly(lactide).

EXAMPLE 16

Effect of Monomer Concentration on Film Modulus

Poly(lactide) was precipitated in methanol from a chloroform solution in order to remove the residual lactide monomer. GPC analysis (the method of Example 1) showed the precipitated polymer to contain 0.0 percentlactide.

The polymer was dissolved in chloroform to make a 10 wt percent solution, and lactide was added back to make 5 separate solutions which, after removing the chloroform, are calculated to produce films containing 0.0, 0.2, 0.4, 1.0 and 4.0 weight percent lactide in poly(lactide). These solutions were solvent cast onto glass, dried overnight at room temperature in a fume hood, and removed to a vacuum oven. The films were hung in the vacuum oven and dried at 30° C. for 72 hours. GPC analysis of the vacuum-dried films showed measured lactide levels of 0.0, 0.0, 0.4, 0.7 and 3.7 wt percent.

The films were then tested for film modulus using ASTM procedure D882.

The results are shown below in Table 20.

TABLE 20

| % Lactide | Tensile (psi avg.) | Std. Dev. | % Elongation | Std. Dev. | Elastic Modulus (psi avg.) | Std. Dev. |
|---|---|---|---|---|---|---|
| 0 | 5490 | 636 | 2.85 | 0.14 | 730,000 | 103,000 |
| 0 | 6070 | 123 | 2.85 | 0.22 | 818,000 | 35,000 |
| 0.4 | 5670 | 227 | 2.75 | 0.27 | 779,000 | 44,000 |
| 0.7 | 5690 | 343 | 4.04 | 1.12 | 749,000 | 58,000 |
| 3.7 | 5570 | 458 | 3.33 | 1.43 | 738,000 | 66,000 |

EXAMPLE 17

Rate of Water Uptake Versus Optical Composition

Samples of poly(lactide), made from 80 percent L-lactide and 20 percent of either D,L-lactide or meso-lactide, were ground to pass a 20 mesh screen. The samples were dried and devolatilized under vacuum then removed to a constant humidity chamber maintained at 24° C. and 50 percent relative humidity. The rate of moisture pick-up was determined gravimetrically, with the final results verified by Karl-Fischer water analysis. The rate of moisture pickup is shown below in Table 21.

TABLE 21

| Time | Parts per Million Weight Gain | |
|---|---|---|
| (Minutes) | L/D,L Polymer | L/Meso Polymer |
| 10 | 600 | 1000 |
| 30 | 1100 | 1500 |
| 60 | 1500 | 1800 |
| 120 | 1600 | 2100 |
| 870 | 2100 | 2600 |
| Final (Karl-Fischer) | 3000 | 2600 |

EXAMPLE 18

Standard Test of Melt Stability

A standard test for determining melt stability is as follows:

A small sample (200 grams or less) of polymer is ground or pelletized and devolatilized by holding under vacuum (about 10 mm Hg) at a temperature of 130° C. or less for 18 hours. At this point the residual lactide content should be 1 wt percent or less. Portions (1–5 grams) of the devolatilized sample are then placed in a 16 ml sample vivial, tightly capped, and placed in a 180° C. oil bath. Samples are removed at times of 15 minutes and 1 hour and analyzed for lactide content by GPC or other appropriate techniques. Lactide which may collect on the cooler portions of the vial is included in the product work-up and test.

Melt-stabilized poly(lactide) will show less than 2 percent lactide in the 15 minute sample, and more preferably less than 2 percent lactide in the 1 hour sample. The most highly stabilized poly(lactide)s will maintain lactide contents of less than 1 percent in both the 15 minute and 1 hour samples, preferably less than 0.5 percent. An unstabilized poly (lactide) may reach the equilibrium lactide content at 180° C. of 3.6 wt percent, or may go even higher as lactide is driven from the polymer melt and collects on the cooler top walls of the vial.

EXAMPLE 19

Water Scavenger Experiments

Dried poly(lactide) pellets were processed in a twin screw extruder to devolatilize and to prepare a portion with 0.5percent by weight of a water scavenger (Stabaxol® P). The strands leaving the extruder are cooled in a water and chopped into pellets. Samples of the control and the test sample were then analyzed by the Karl Fischer technique for moisture content, with no drying. The control sample contained 1700 ppm water, the test sample had 450 ppm water. The control sample was then dried under nitrogen at 40° C., reducing the water content to 306 ppm. A vacuum-dried control sample had 700 ppm water.

The as-produced test sample and the dried control samples were then processed in a ½" single screw extruder (Brabender®) at 160° C., with a retention time of 3 minutes. The number average molecular weight for the dried control sample dropped from an initial value of 44,000 to a final value of 33,000 for the 306 ppm water sample and to 28,000 for the 700 ppm water sample. The test sample number average molecular weight dropped from an initial value of 40,000 to a final value of 33,000.

This sample shows how the water scavenger protected the polymer from moisture pick-up, imparting the same stability as a thorough drying of the control sample. Combining a water scavenger with appropriate drying is expected to give even greater stability. cl EXAMPLE 20

Optimization of Catalyst Concentration

A mixture of 80 percent L-lactide and 20 percent D,L-lactide was polymerized using three different levels of tin(II) bis(2-ethyl hexanoate) catalyst. Batches were prepared at initial monomer/catalyst molar ratios of 1000:1, 3000:1, and 20,000:1. polymerization times were adjusted to reach high conversion without being excessively long and thereby causing degradation in the melt. The reaction times were 1,2 and 20 hours, respectively. The polymerization temperature was 180° C. The polymers were ground to a coarse powder and devolatilized at 125° C. and 10 mm Hg overnight. The samples were then reground and 1-gram portions of each were placed into silanized vials, 16 ml capacity. The vials were sealed and placed into an oil bath at 180° C. Vials were then removed at various times and the samples were analyzed by GPC after dissolution in chloroform. The molecular weights and lactide contents are shown below in Table 22.

TABLE 22

| Sample | Time (min) | Number Average Molecular Weight | Weight Average Molecular Weight | Lactide Weight % |
|---|---|---|---|---|
| 1000:1 | 0 | 39,000 | 81,300 | 0.8 |
|  | 5 | 28,100 | 57,300 | 2.4 |
|  | 15 | 25,800 | 49,700 | 2.8 |
|  | 30 | 23,100 | 43,800 | 3.7 |
|  | 60 | 22,800 | 43,200 | 3.6 |
| 3000:1 | 0 | 53,100 | 113,600 | 0.6 |
|  | 5 | 39,000 | 76,400 | 0.4 |
|  | 15 | 30,300 | 65,400 | 1.9 |
|  | 30 | 29,000 | 60,400 | 2.7 |
|  | 60 | 28,200 | 55,200 | 2.8 |
| 20000:1 | 0 | 89,200 | 184,000 | 0.0 |
|  | 5 | 81,200 | 165,100 | 0.0 |
|  | 15 | 54,300 | 134,600 | 0.1 |
|  | 30 | 51,100 | 119,600 | 0.0 |
|  | 60 | 49,500 | 111,000 | 0.0 |

These results show the benefit of optimizing the catalyst level used in the polymerization process. Note that both lactide reformation and molecular weight retention benefits are realized from the reduced catalyst levels (higher monomer/catalyst ratio).

It is believed catalyst levels should be limited to 1000:1 for the high end of catalyst usage, with 3000:1 being more preferable and showing somewhat improved stability. Lower levels still, such as 20000:1, show greatly improved stability. Beyond this level it is believed the polymerization rates become too slow to be practical.

EXAMPLE 21

Removal of Tin Catalyst from Poly(lactide) by Precipitation 45 grams of L-lactide and 13 grams of D,L-lactide were charged with 78 milligrams of crystalline lactic acid to a 200 ml round bottom flask. This was heated to 180° C. with magnetic stirring in an oil bath and blanketed with dry nitrogen. Catalyst in the form of tin(II) bis(2-ethyl hexanoate) was added as 0.20 ml of a 0.47 g/ml solution in THF after the molten lactide was at temperature. The mixture was allowed to stir for one minute and then pipetted into 3 silanized glass vials, which were then sealed and placed into a 180° C. oil bath for 75 minutes. The vials were allowed to cool and the polymer recovered by breaking the glass. The polymer was ground to a coarse powder and dissolved in chloroform to make a 10 percent solution. The polymer contained 3.8 percent residual monomer and had a number average molecular weight of 70,000 as determined by GPC measurement (the method of Example 9). 500 ml of methanol were placed in a 1-liter glass blender flask. The blender was turned on to medium speed and 50 ml of the polymer in chloroform solution was poured in over a period of three minutes. After one additional minute of blending the mixture was filtered, then rinsed with 100 ml of methanol, and dried overnight under vacuum. The polymer consisted of a fibrous mat. It contained 0.3 percent residual monomer and had a number average molecular weight of 66,900.

The measured tin level in the precipitated polymer was 337 ppm by weight, compared to a calculated value of 466 ppm for the as-produced polymer. This result indicates the feasibility of reducing residual catalyst levels in lactide polymers by solvent precipitation with the benefit of improved stability as detailed in Example 20.

EXAMPLE 22

Samples of devolatilized poly(lactide) were tested in a Rosand Model 14° C. capillary rheometer. The die was 1 mm diameter and 16 mm long, with an entry angle of 180°. The table below gives the pressure drop across the die as a function of nominal shear rate (not Rabinowitsch corrected) for various molecular weights and temperatures.

TABLE 23

| Mn | MW | Temp. (°C.) | Nominal shear rate (s$^{-1}$) | Pressure Drop (MPa) |
|---|---|---|---|---|
| Results at 150° C. | | | | |
| 34,000 | 70,000 | 150 | 192 | 2.0 |
|  |  |  | 384 | 5.5 |
|  |  |  | 960 | 10.0 |
|  |  |  | 1920 | 13.8 |
|  |  |  | 4800 | 19.7 |
|  |  |  | 9600 | 23.7 |
| 52,000 | 108,000 | 150 | 192 | 9.9 |
|  |  |  | 384 | 15.6 |
|  |  |  | 960 | 19.9 |
|  |  |  | 1920 | 23.9 |
|  |  |  | 4800 | 29.4 |
|  |  |  | 9600 | — |
| 60,000 | 137,000 | 150 | 192 | 7.4 |
|  |  |  | 384 | 11.1 |
|  |  |  | 960 | 16.6 |
|  |  |  | 1920 | 21.0 |
|  |  |  | 4800 | — |
|  |  |  | 9600 | — |
| 183,000 | 475,000 | 150 | 192 | 19.1 |
|  |  |  | 384 | 27.0 |
|  |  |  | 960 | 31.4 |
|  |  |  | 1920 | — |
|  |  |  | 4800 | — |
|  |  |  | 9600 | — |
| Results at 175° C. | | | | |
| 34,000 | 70,000 | 175 | 192 | 0.4 |
|  |  |  | 384 | 0.5 |
|  |  |  | 960 | 3.4 |
|  |  |  | 1920 | 5.5 |
|  |  |  | 4800 | 9.2 |
|  |  |  | 9600 | 12.5 |
| 52,000 | 108,000 | 175 | 192 | 2.2 |
|  |  |  | 384 | 4.6 |
|  |  |  | 960 | 7.6 |
|  |  |  | 1920 | 11.5 |
|  |  |  | 4800 | 17.2 |
|  |  |  | 9600 | 22.1 |
| 183,000 | 475,000 | 175 | 192 | 11.5 |
|  |  |  | 384 | 16.6 |
|  |  |  | 960 | 20.2 |
|  |  |  | 1920 | 24.4 |
|  |  |  | 4800 | 29.9 |
|  |  |  | 9600 | — |
| Results at 200° C. | | | | |
| 60,000 | 137,000 | 200 | 192 | 0.5 |
|  |  |  | 384 | 1.6 |
|  |  |  | 960 | 3.3 |
|  |  |  | 1920 | 5.3 |
|  |  |  | 4800 | — |
|  |  |  | 9600 | 13.2 |
| 183,000 | 475,000 | 200 | 192 | 7.0 |
|  |  |  | 384 | 11.0 |
|  |  |  | 960 | 14.2 |
|  |  |  | 1920 | 17.9 |
|  |  |  | 4800 | 21.6 |
|  |  |  | 9600 | — |

EXAMPLE 23

Effect of Meso-lactide Concentration on Rate of Crystallization

Polymer samples of various optical composition were prepared by polymerizing mixtures of L-lactide and meso-lactide with Tin II bis(2-ethyl hexanoate) catalyst at a temperature of about 180° C. A portion of each sample was tested in a Mettler Differential Scanning Calorimeter Model 30 (DSC) by heating from 20° C. to 200° C. at 20° C./minute. The sample was then held at 200° C. for 2 minutes to completely melt any crystals. The sample was thereafter rapidly quenched and reheated with the same procedure. The rapid heat-ups in this method allow a limited time for crystallization to occur, allowing differences in crystallization rates to be observed. Results are shown in the table below.

TABLE 24

| Sample % meso | Exotherm (J/gm) | Peak Temp. (°C.) | Endotherm (J/gm) | Peak Temp. (°C.) |
|---|---|---|---|---|
| First upheat | | | | |
| 0 | 29.1 | 114 | 33.7 | 172 |
| 3 | 44 | 126 | 5.9 | 159 |
| 6 | 0 | — | 0 | — |
| 9 | 0 | — | 0 | — |
| Second upheat | | | | |
| 0 | 14.1 | 137 | 12.2 | 173 |
| 3 | 0 | — | 0 | — |
| 6 | 0 | — | 0 | — |
| 9 | 0 | — | 0 | — |

The results show that the rate of crystallization for the polymer is decreased dramatically with the addition of small amounts of meso-lactide to the polymerization mixture.

EXAMPLE 24

The Effect of Meso-lactide Concentration on Crystallization

Samples of devolatilized poly(lactide) of varying optical composition and with number average molecular weights in the range of 50,000 to 130,000 were prepared in a continuous pilot plant. The samples were dissolved in chloroform to a concentration of 5 grams/100 cc and the optical rotation of the samples was measured to determine the concentration of meso-lactide which had been present in the monomer mixture prior to polymerization. Separate optical rotation and gas chromatography analysis of the monomer mixture confirmed that L-lactide and meso-lactide are the predominate components when meso-lactide is present at a concentration of 20 percent or less, and only a small correction is required for D-lactide.

Additional samples were made by polymerizing mixtures with known weights of L-lactide and meso-lactide.

All samples were subjected to an annealing procedure to develop crystallinity. The annealing procedure consisted of placing the samples in an oven at 100°–105° C. for 90 minutes, then lowering the temperature 10° C. each ½ hour until the temperature reached 45° C. The oven was then shut off and the samples were allowed to cool to room temperature. The energy of the melting endotherm and the peak melting temperature were then measured using a Mettler Differential Scanning Calorimeter (DSC) apparatus with a scan speed of 20° C. minute. The energy of melting is a measure of crystallinity in the annealed samples.

FIG. 3 shows the sharp decline in potential crystallinity between 9 and 12 percent meso content.

In contrast, a polymer sample made by polymerizing 80 percent L-lactide and 20 percent D,L-lactide showed, after annealing, a melting endotheim of 12.3 J/gm. This composition has the same enantiomeric excess in terms of lactide acid R- and S- unit as does an 80 percent L-lactide/20 percent meso-lactide blend. The 20 percent meso-lactide containing blend showed no crystallinity after annealing, as shown by FIG. 3.

EXAMPLE 25

Effect of Plasticizer on Crystallization Rate

Devolatilized polymer samples from a continuous pilot plant were compounded with dioctyl adipate (a plasticizing agent) and/or silica with a twin screw extruder. The samples were then tested for nucleation rates using the DSC method of Example 23. The table below shows that dioctyl adipate (DOA) can increase the rate of crystallization of poly (lactide) or of a filled poly(lactide).

TABLE 25

| Sample | Exotherm (J/gm) | Peak Temp. (°C.) | Endotherm (J/gm) | Peak Temp. (°C.) |
|---|---|---|---|---|
| Base polymer | 0 | — | 1.3 | 143 |
| Base polymer + 8 wt % DOA | 24.6 | 84 | 22.1 | 147 |
| Base polymer + 40 wt % silica + | 2.4 | 86 | 3.9 | 149 |
| Base polymer + 40 wt % silica + 5 wt % DOA | 14.9 | 86 | 15.4 | 147 |
| Second upheat | | | | |
| Base polymer | 0 | — | 0 | — |
| Base polymer + 8 wt % DOA | 25.0 | 98 | 24.0 | 143 |
| Base polymer + 40 wt % silica + | 0 | — | 0 | — |
| Base polymer + 40 wt % silica + 5 wt % DOA | 15.2 | 97 | 14.6 | 143 |

EXAMPLE 26

An Evaluation of Nucleating Agents

A devolatilized sample of poly(lactide) polymer was compounded with a variety of potential nucleating agents in a single screw extruder. The candidate nucleating agents were added at a nominal level of 5 percent by weight. The single screw extruder is not as effective of a mixer as would be used commercially, so failure to observe an effect in these tests does not mean that a candidate agent would not be effective if blended more thoroughly. A positive result in this test demonstrates potential ability to increase crystallization rates. Additives which increased crystallinity in the second upheat (on a quenched sample) were rated ++, additives which showed an effect only on the first upheat were rated +, and additives which showed no effect were rated 0.

TABLE 26

| Additive | Effect |
|---|---|
| None | 0 |
| talc, MP1250 (Pfizer) | ++ |
| 3-nitro benzoic acid | 0 |
| saccharin, sodium salt | ++ |
| terephthalic acid, disodium salt | 0 |
| calcium silicate, −200 mesh | + |
| sodium benzoate | + |
| calcium titanate, −325 mesh | + |
| boron nitride | + |

TABLE 26-continued

| Additive | Effect |
|---|---|
| calcium carbonate, 0.7 micron | 0 |
| copper phthalocyanine | + |
| saccharin | 0 |
| low molecular weight polyethylene | 0 |
| talc, Microtuff-F (Pfizer) | ++ |
| talc, Ultratalc (Pfizer) | ++ |
| ethylene acrylic acid sodium ionomer (Allied Signal) | 0 |
| isotactic polypropylene | + |
| polyethylene terephthalate | 0 |
| low molecular weight poly(L-lactide) | ++ |
| Millad 3940 (Milliken) | ++ |
| Millad 3905 (Miliken) | + |
| NC-4 (Mitsui) | + |
| polybutylene terephthalate | + |
| talc in polystyrene (Polycom Huntsman) | + |
| talc in polyethylene (Advanced Compounding) | ++ |

EXAMPLE 27

Orientation and Rate of Crystallization

DSC was used to determine the effectiveness of orientation as a method of increasing the rate of crystallization. The method used is the same as in Example 23. An oriented sample will increase crystallization rate primarily on the first upheat. The second upheat, which is on a sample that has been melted and quenched and therefore is no longer oriented is not expected to show crystallization. The results in the table below show an increase in crystallization rate for the nonwoven fibers of Examples 3 and 4. The melting and quenching procedure (heating at 200° C. for 2 minutes, followed by rapid cooling) reduced the crystallization rate, although the effect of orientation did not disappear. It is believed that a longer hold time in the melt would eliminate the effect of orientation.

TABLE 27

| Sample | Exotherm (J/gm) | Peak Temp. (°C.) | Endotherm (J/gm) | Peak Temp. (°C.) |
|---|---|---|---|---|
| First upheat | | | | |
| Feed pellet from Example 3 | 0 | — | 0.6 | 147 |
| Nonwoven, Example 3 | 19.4 | 120 | 19.7 | 150 |
| Feed pellet from Example 4 | 0 | — | 0.2 | 169 |
| Nonwoven, Example 4 | 22.8 | 118 | 21.5 | 148 |
| Second upheat | | | | |
| Feed pellet from Example 3 | 0 | — | 0 | — |
| Nonwoven, Example 3 | 10.5 | 127 | 9.6 | 148 |
| Feed pellet from Example 4 | 0 | — | 0 | — |
| Nonwoven, Example 4 | 7.1 | 125 | 7.5 | 146 |

It will be understood that even though these numerous characteristics and advantages of the invention have been set forth in the foregoing description, together with details of the structure and function of the invention, the disclosure is illustrative only, and changes may be made in detail, especially in matters of shape, size and arrangement of the parts or in the sequence or the timing of the steps, within the broad principle of the present invention to the full extent indicated by the broad general meaning of the terms in which the appended claims are expressed.

What is claimed:

1. A nonwoven fabric comprising:
   (a) a plurality of fibers, at least a first portion of which comprise fibers including a first melt stable polymer composition having a number average molecular weight of from about 10,000 to about 300,000;
      (i) said first polymer composition having a lactide monomer concentration of less than about 2% by weight;
      (ii) said first polymer composition being formed from at least meso-lactide and remaining lactide; said remaining lactide being selected from the group consisting of L-lactide, D-lactide and mixtures thereof; and
      (iii) said. first polymer composition being formed from a reaction mixture comprising about 0.5% to about 50% by weight meso-lactide based on the total amount of meso-lactide and remaining lactide;
   (b) said first polymer composition being in a form such that an isolated and devolatilized sample, prior to incorporation into said fibers, would form less than 1% by weight lactide upon heating at 180° C. for 1 hour.

2. A nonwoven fabric according to claim 1 wherein:
   (a) said first polymer composition is formed from at least: meso-lactide; remaining lactide; and, epoxidized oil.

3. A nonwoven fabric according to claim 2 wherein:
   (a) said first melt stable polymer composition has a number average molecular weight of from about 50,000 to about 250,000.

4. A nonwoven fabric according to claim 2 wherein:
   (a) said first polymer composition is formed from a reaction mixture comprising about 12% to about 50% by weight meso-lactide, based on the total amount of meso-lactide and remaining lactide.

5. A nonwoven fabric according to claim 2 wherein:
   (a) said first melt stable polymer composition has a water concentration, if water is present at all, of less than about 500 parts per million.

6. A nonwoven fabric according to claim 2 wherein:
   (a) said first polymer composition is formed from meso-lactide; remaining lactide; epoxidized oil; and, antioxidant stabilizing agent.

7. A nonwoven fabric according to claim 2 wherein:
   (a) said first portion of fibers comprise melt blown fibers.

8. A nonwoven fabric according to claim 2 wherein:
   (a) said first portion of fibers comprise spunbond fibers.

9. A nonwoven fabric according to claim 2 wherein:
   (a) said first polymer composition includes organic filler.

10. A nonwoven fabric according to claim 2 wherein:
    (a) said first polymer composition includes pigment.

11. A nonwoven fabric according to claim 2 wherein:
    (a) said first portion of fibers comprise a semi-crystalline polymer composition.

12. A nonwoven fabric according to claim 11, wherein:
    (a) said first polymer composition is formed from a reaction mixture comprising less than about 12% by weight meso-lactide, based on the total amount of meso-lactide and remaining lactide.

13. A nonwoven fabric according to claim 1 wherein:
    (a) said first polymer composition is formed from: meso-lactide, remaining lactide and at least one other component capable of reacting into the polymer.

14. A nonwoven fabric according to claim 13 wherein:
(a) said at least one other component capable of reacting into the polymer comprises molecules having at least two sites for reaction into the polymer.

15. A nonwoven fabric according to claim 14 wherein:
(a) said molecules having at least two sites for reaction into the polymer include molecules having at least three sites for reaction into the polymer.

16. A nonwoven fabric according to claim 15 wherein:
(a) said component having molecules with at least three sites for reaction to the polymer comprises a triol.

17. A nonwoven fabric comprising:
(a) a plurality of fibers, at least a first portion of which comprise fibers formed from a melt stable first polymer composition having a number average molecular weight of from about 10,000 to about 300,000;
  (i) said first polymer composition having a lactide monomer concentration of less than about 2% by weight;
  (ii) said first polymer composition including polymer chains comprising monomer units derived from at least meso-lactide; and, L-lactide; and,
  (iii) said first polymer composition being formed from a reaction mixture comprising about 0.5% to about 50% by weight meso-lactide, based on the total amount of meso-lactide, L-Lactide and, if present, D-lactide; and
(b) said first polymer composition being in a form such that an isolated and devolatilized sample of it, prior to incorporation into said fibers, would form less than 1% by weight lactide, upon heating at 180° C. for 1 hour.

18. A nonwoven fabric according to claim 17 wherein:
(a) said polymer composition includes polymer chains comprising units derived from at last one additional material to meso-lactide and L-lactide.

19. A nonwoven fabric according to claim 18 wherein:
(a) said at least one additional material is D-lactide.

20. A process for preparing a nonwoven fabric; said process including steps of:
(a) melt processing a melt stable first polymer composition into fibers; said first polymer composition having a number average molecular weight of from about 10,000 to about 300 000;
  (i) said first polymer composition, during said step of melt processing, having a lactide concentration of less than about 2% by weight and a concentration of water, if present at all, of less than about 2000 parts per million;
  (ii) said first polymer composition being formed from at least meso-lactide and remaining lactide; said remaining lactide being selected from the group consisting of L-lactide, D-lactide and mixtures thereof; said polymer composition being formed from a reaction mixture comprising about 0.5% to about 50% by weight meso-lactide, based on the total amount of meso-lactide and remaining lactide; and,
  (iii) said step of melt processing a melt stable first polymer composition further comprising melt processing a polymer composition formed from epoxidized oil; and,
(b) forming the fibers, made from melt processing of the melt stable polymer composition, into a nonwoven fabric.

21. A process according to claim 20 wherein:
(a) said step of melt processing to form fibers comprises a step of melt blowing fibers.

22. A process according to claim 20 wherein:
(a) said step of melt processing to form fibers comprises a step of forming spunbond fibers.

* * * * *

UNITED STATES PATENT AND TRADEMARK OFFICE
CERTIFICATE OF CORRECTION

PATENT NO. : 5,807,973

DATED : SEPTEMBER 15, 1998

INVENTOR(S) : GRUBER ET AL.

It is certified that error appears in the above-identified patent and that said Letters Patent is hereby corrected as shown below:

Col. 5, line 40: insert —:— after "enhanced adhesion"

Col. 5, line 49: insert —.— after "adhesion"

Col. 6, line 1: "also may" should read —is a—

Col. 9, line 21: "meso–lactide lactide with" should read —meso–lactide with—

Col. 12, line 53: "events" should read —agents—

Col. 12, line 61: "SnCl$_2$SnBr$_2$" should read —SnCl$_2$, SnBr$_2$—

Col. 13, line 4: "(2-ethyi hexanoate)" should read —(2-ethyl hexanoate)—

Col. 13, line 9: "(butyltin" should read —dibutyltin—

Col. 13, line 14: "depolymerizations" should read —depolymerization—

Col. 15, line 5: "examples" should read —example,—

Col. 15, line 26: insert —.— after "pipeline (9)"

Col. 18, line 59: "11.57 pm" should read —11.57 μm—

Col. 19, line 28: insert —pellets.— after "chopped into"

Col. 19, line 29: "20 C./minutes" should read —20°C./minute—

Col. 20, lines 8-9: "poly(lactitemperatureerent temperatures" should read —poly(lactide) at different temperatures—

UNITED STATES PATENT AND TRADEMARK OFFICE
CERTIFICATE OF CORRECTION

| | |
|---|---|
| PATENT NO. : | 5,807,973 |
| DATED : | SEPTEMBER 15, 1998 |
| INVENTOR(S) : | GRUBER ET AL. |

It is certified that error appears in the above-identified patent and that said Letters Patent is hereby corrected as shown below:

Col. 26, line 26: "1.80° C" should read —180° C—

Col. 30, line 41: "being, Lore" should read —being more—

Col. 31, line 7: "percentlactide" should read —percent lactide—

Col. 32, line 4: "vivial" should read —vial—

Col. 32, lines 25-26: —0.5percent" should read —0.5 percent—

Col. 32, line 27: insert "trough" between "water" and "and"

Col. 32, line 49: start a new paragraph after "stability."

Col. 32, line 49: "cl EXAMPLE 20" should read —EXAMPLE 20—

Col. 32, line 56: "polymerization" should read —Polymerization—

Col. 33, line 49: start a new paragraph at "500 ml of methanol..."

Signed and Sealed this

Thirteenth Day of June, 2000

*Attest:*

Q. TODD DICKINSON

*Attesting Officer*     *Director of Patents and Trademarks*